(12) United States Patent
Goto

(10) Patent No.: US 10,824,919 B1
(45) Date of Patent: Nov. 3, 2020

(54) BLOOD VESSEL DETECTING APPARATUS, MAGNETIC RESONANCE IMAGING APPARATUS, AND PROGRAM

(71) Applicant: GENERAL ELECTRIC COMPANY, Schenectady, NY (US)

(72) Inventor: Takao Goto, Tokyo (JP)

(73) Assignee: General Electric Company, Schenectady, NY (US)

( * ) Notice: Subject to any disclaimer, the term of this patent is extended or adjusted under 35 U.S.C. 154(b) by 259 days.

(21) Appl. No.: 16/094,614

(22) PCT Filed: Apr. 18, 2017

(86) PCT No.: PCT/US2017/028105
§ 371 (c)(1),
(2) Date: Oct. 18, 2018

(87) PCT Pub. No.: WO2017/184585
PCT Pub. Date: Oct. 26, 2017

(30) Foreign Application Priority Data

Apr. 21, 2016 (JP) .................. 2016-085200

(51) Int. Cl.
*G06K 9/62* (2006.01)
*A61B 5/00* (2006.01)
(Continued)

(52) U.S. Cl.
CPC .............. *G06K 9/628* (2013.01); *A61B 5/055* (2013.01); *A61B 5/489* (2013.01); *A61B 5/7264* (2013.01);
(Continued)

(58) Field of Classification Search
None
See application file for complete search history.

(56) References Cited

U.S. PATENT DOCUMENTS

2006/0110018 A1   5/2006 Chen et al.
2010/0119136 A1   5/2010 Itagaki et al.
(Continued)

FOREIGN PATENT DOCUMENTS

JP   2009-261904   11/2009
JP   2015-023944   2/2015

OTHER PUBLICATIONS

Goto et al., "Automated SmartPrep Tracker Positioning in Liver MRI Scans,"Medical imaging Technology, vol. 31, No. 2, Mar. 2013, p. 105-112.
(Continued)

*Primary Examiner* — Jiangeng Sun

(57) ABSTRACT

An MRI apparatus 1 comprising an image producing unit 101 for producing a plurality of axial images $D_1$ to $D_{10}$ in a plurality of slices defined in a body part to be imaged containing a blood vessel; a classifying unit 102 for classifying the plurality of axial images $D_1$ to $D_{10}$ into a plurality of classes I to IV based on which a portion of the imaged body part each of the plurality of axial images $D_1$ to $D_{10}$ represents; and a defining unit 103 for defining a search region for searching for a blood vessel from within an axial image based on within which of the plurality of classes I to IV the axial image falls.

9 Claims, 34 Drawing Sheets

(51) Int. Cl.
    *G01R 33/483*    (2006.01)
    *G01R 33/56*     (2006.01)
    *G06K 9/20*      (2006.01)
    *A61B 5/055*     (2006.01)

(52) U.S. Cl.
    CPC ..... *G01R 33/4835* (2013.01); *G01R 33/5608* (2013.01); *G06K 9/2054* (2013.01); *G06K 2209/051* (2013.01)

(56) References Cited

U.S. PATENT DOCUMENTS

| | | |
|---|---|---|
| 2011/0026798 A1 | 2/2011 | Madabhushi et al. |
| 2012/0071156 A1 | 10/2012 | Bi et al. |
| 2013/0202173 A1 | 8/2013 | Buckler et al. |
| 2015/0073535 A1* | 3/2015 | Consigny ................ A61L 31/10 623/1.38 |
| 2015/0245776 A1* | 9/2015 | Hirohata ................ A61B 5/026 600/504 |
| 2016/0296208 A1* | 10/2016 | Sethuraman ......... A61B 8/5207 |
| 2016/0358333 A1* | 12/2016 | Lee .......................... G06T 7/68 |

OTHER PUBLICATIONS

International Search Report and Written Opinion for PCT/US2017/028105, dated Jun. 21, 2017, 10 pages.

\* cited by examiner $$MA = \begin{pmatrix} & \alpha_1 & \alpha_2 & \alpha_3 & \cdots & \alpha_k \\ \alpha_1 & 0 & d_{12} & d_{13} & \cdots & d_{1k} \\ \alpha_2 & d_{21} & 0 & d_{23} & \cdots & d_{2k} \\ \alpha_3 & d_{31} & d_{32} & 0 & \cdots & d_{3k} \\ \vdots & \vdots & \vdots & \vdots & \ddots & \vdots \\ \alpha_k & x_{k1} & x_{k2} & x_{k3} & \cdots & 0 \end{pmatrix}$$

FIG. 12

BLOOD VESSEL DETECTING APPARATUS, MAGNETIC RESONANCE IMAGING APPARATUS, AND PROGRAM

CROSS-REFERENCE TO RELATED APPLICATIONS

This application is a filing under 35 U.S.C. 371 of international application number PCT/US2017/028105, filed Apr. 18, 2017, which claims priority to Japanese Patent Application No. 2016-085200, filed on Apr. 21, 2016, the entirety of both disclosures are hereby incorporated by reference.

BACKGROUND

The present invention relates to a blood vessel detecting apparatus for detecting a blood vessel, a magnetic resonance imaging apparatus comprising the blood vessel detecting apparatus, and a program applied to the blood vessel detecting apparatus.

Magnetic resonance imaging apparatuses for imaging a subject using a contrast medium are known.

An example of the method of imaging a subject using a contrast medium is one in which an operator produces an image in each of a plurality of axial planes intersecting a torso, visually finds a position of an aorta from within/among an image/images, and defines a tracker region for detecting the contrast medium at the position of the aorta.

An aorta is detected by increasing the area of a $Z_{dephaser}$ in a slice gradient magnetic field to diminish as much as possible signals from blood in the aorta rendered in an axial image. Blood in the aorta, however, sometimes exhibits high signals in cardiac systole because the blood flow velocity in the aorta lowers then. Therefore, in practice, signals from blood in the aorta sometimes cannot be fully diminished due to an effect of the high-signal blood. This poses a problem that a tissue different from the aorta is wrongly detected as an aorta, or the aorta cannot be detected. Accordingly, there has been disclosed a technique capable of detecting a position of the aorta even when signals from blood in the aorta are not fully diminished.

The above-referenced technique is capable of detecting a position of the aorta even when signals from blood in the aorta are not fully diminished. In some axial images, however, a cross section of a body part, different from the cross section of the aorta of interest to be detected, may exhibit a signal pattern resembling that of the aorta. In this case, the cross section of the body part different from the aorta may be wrongly detected as a cross section of an aorta. When the aorta is wrongly detected, a tracker is defined at a position offset from the aorta, resulting in a problem that accuracy in detecting a contrast medium is deteriorated.

Accordingly, there is a need for developing a technique for improving the accuracy of detection of a blood vessel in an image.

SUMMARY

In a first aspect, is a blood vessel detecting apparatus comprising an image producing unit for producing a plurality of images in a plurality of slices defined in a body part to be imaged containing a blood vessel; a classifying unit for classifying said plurality of images into a plurality of classes based on which portion in said imaged body part each of said plurality of images represents; and a defining unit for defining a search region for searching for said blood vessel from within said image based on within which of said plurality of classes said image falls.

The present invention, in its second aspect, is a magnetic resonance imaging apparatus comprising scanning section for performing a scan on a body part to be imaged containing a blood vessel, said apparatus comprising the blood vessel detecting apparatus in the first aspect.

The present invention, in its third aspect, is a program for causing a computer to execute image producing processing of producing a plurality of images in a plurality of slices defined in a body part to be imaged containing a blood vessel; classifying processing of classifying said plurality of images into a plurality of classes based on which portion in said imaged body part each of said plurality of images represents; and defining processing of defining a search region for searching for said blood vessel from within said image based on within which of said plurality of classes said image falls.

A plurality of images are classified into a plurality of classes, and a search region for searching for the blood vessel from within an image is defined according to within which of the plurality of classes the image falls; thus, accuracy of detection of a blood vessel within an image may be improved.

BRIEF DESCRIPTION OF THE DRAWINGS

FIG. 12 is a diagram schematically showing an adjacency matrix MA;

DETAILED DESCRIPTION

Now embodiments for practicing the invention will be described hereinbelow, although the present invention is not limited thereto.

Figure 1:
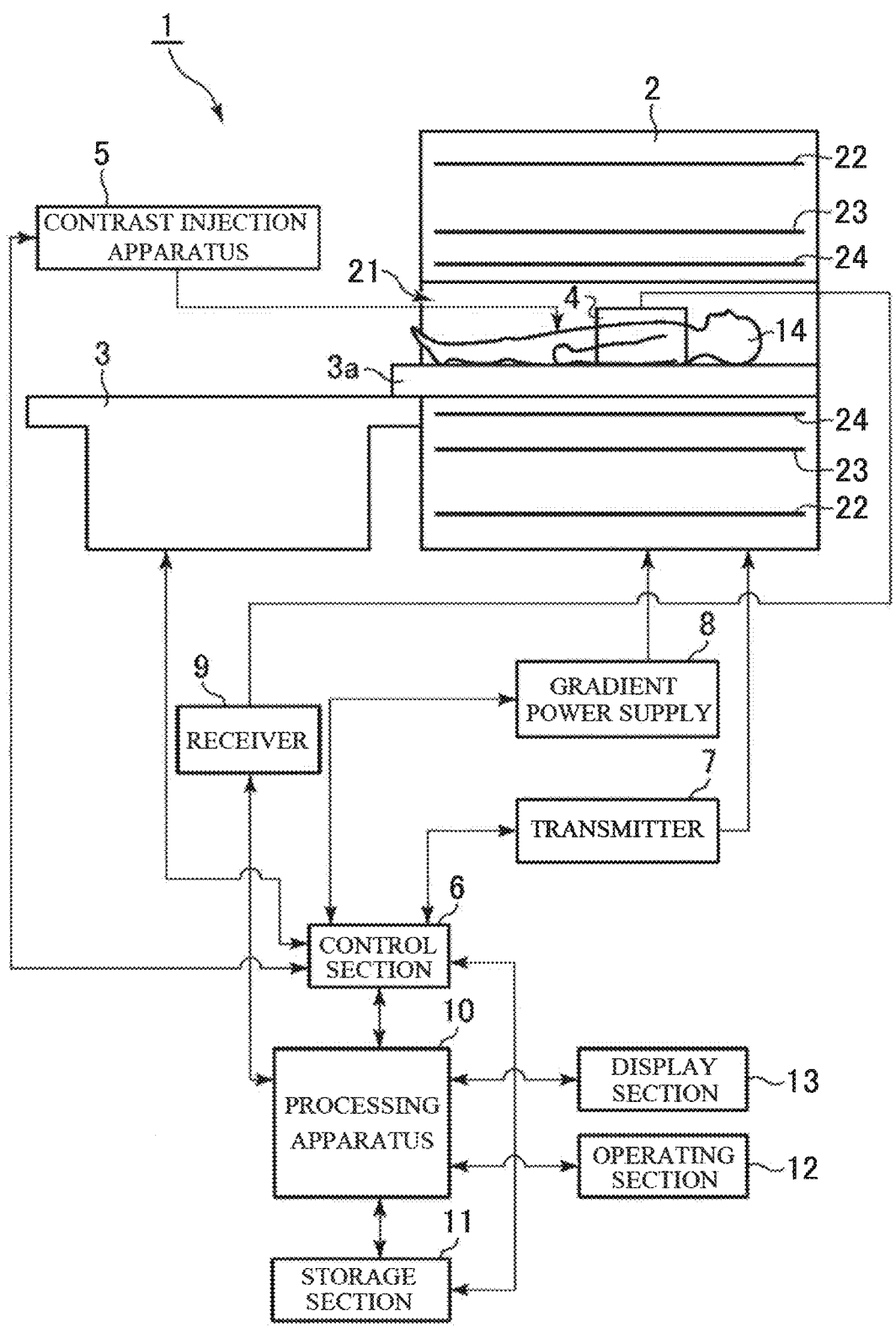
FIG. 1 is a schematic diagram of a magnetic resonance imaging apparatus in one embodiment of the present invention.

FIG. 1 is a schematic diagram of a magnetic resonance imaging apparatus in one embodiment of the present invention. The magnetic resonance imaging apparatus (referred to as "MRI apparatus" hereinbelow) 1 comprises a magnet 2, a table 3, a receive coil 4, and a contrast injection apparatus 5.

The magnet 2 has a reception space 21 in which a subject 14 is received. Moreover, the magnet 2 has a superconductive coil 22, a gradient coil 23, and an RF coil 24. The superconductive coil 22 applies a static magnetic field, the gradient coil 23 applies a gradient pulse, and the RF coil 24 applies an RF pulse. A permanent magnet may be employed in place of the superconductive coil 22.

The table 3 has a cradle 3a for carrying the subject 14. It is by the cradle 3a that the subject 14 is carried into the reception space 21.

The receive coil 4 is attached to the subject 14. The receive coil 4 receives magnetic resonance signals from the subject 14. The contrast injection apparatus 5 injects a contrast medium into the subject 14.

The MRI apparatus 1 further comprises a control section 6, a transmitter 7, a gradient power supply 8, a receiver 9, a processing apparatus 10, a storage section 11, an operating section 12, and a display section 13.

The control section 6 receives from the processing apparatus 10 data containing waveform information, the time for application, etc. of the RF pulse and gradient pulse used in a sequence. The control section 6 then controls the transmitter 7 based on the data for the RF pulse, and controls the gradient power supply 8 based on the data for the gradient pulse. The control section 6 also performs control of the start time for injection of the contrast medium by the contrast injection apparatus 5, control of movement of the cradle 3a, etc. While the control section 6 performs control of the contrast injection apparatus 5, transmitter 7, gradient power supply 8, cradle 3a, etc. in FIG. 1, the control of the contrast injection apparatus 5, transmitter 7, gradient power supply 8, cradle 3a, etc. may be performed by a plurality of control sections. For example, there may be separately provided a control section for controlling the contrast injection apparatus 5, that for controlling the transmitter 7 and gradient power supply 8, and that for controlling the cradle 3a.

The transmitter 7 supplies electric current to the RF coil 24 based on the data received from the control section 6. The gradient power supply 8 supplies electric current to the gradient coil 23 based on the data received from the control section 6.

The receiver 9 applies processing, such as demodulation/detection, to magnetic resonance signals received by the receive coil 4, and outputs the resulting signals to the processing apparatus 10. It should be noted that a combination of the magnet 2, receive coil 4, control section 6, transmitter 7, gradient power supply 8, and receiver 9 constitute the scanning section.

Figure 2:
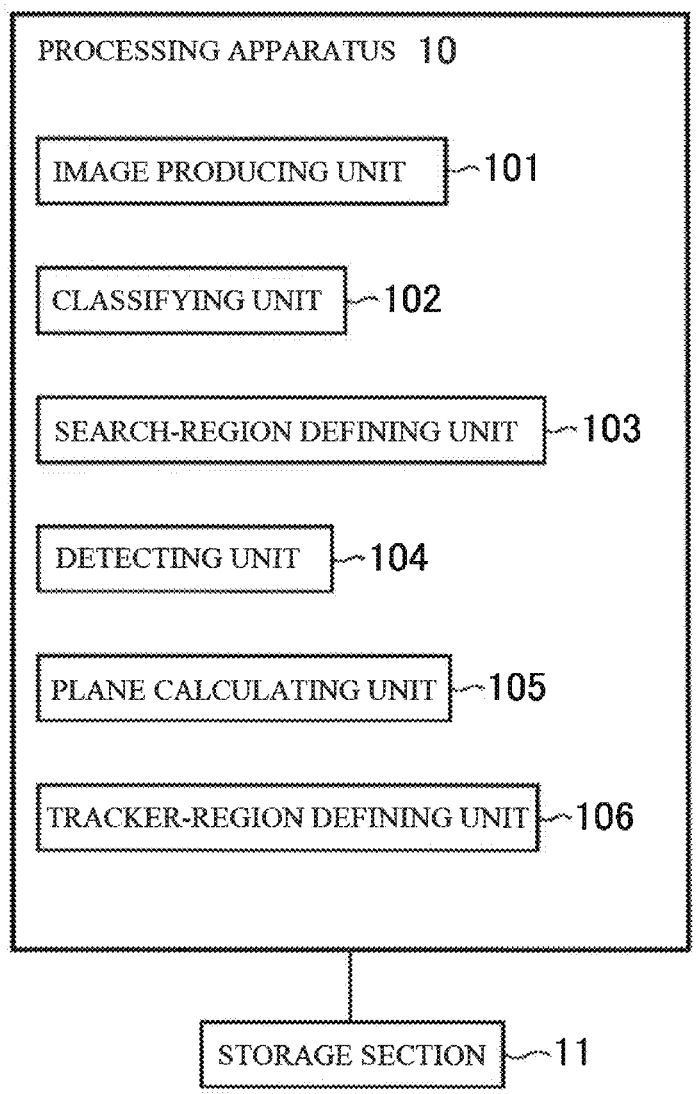
FIG. 2 is a diagram explaining unit the processing apparatus 10 implements.

The storage section 11 stores therein programs executed by the processing apparatus 10, and the like. The storage section 11 may be a non-transitory storage medium, such as a hard disk or CD-ROM. The processing apparatus 10 loads a program stored in the storage section 11, and operates as a processor executing processing written in the program. By executing the processing written in the program, the processing apparatus 10 implements several kinds of units. FIG. 2 is a diagram explaining the units the processing apparatus 10 implements.

Image producing unit 101 produces an image in each of a plurality of slices intersecting a body part to be imaged in the subject 14.

Classifying unit 102 classifies the plurality of images into a plurality of classes based on which portion in the imaged body part each of the plurality of images obtained by the image producing unit 101 represents. The class will be discussed later.

Search-region defining unit 103 defines a search region for searching for a blood vessel on an image-by-image basis based on within which of the plurality of classes each of the plurality of images falls.

Detecting unit 104 detects a position of an aorta from within the search region. Plane calculating unit 105 calculates a plane longitudinally cutting the aorta based on positions PA1 to PA10 (see FIG. 31) of the aorta A detected by the detecting unit 104.

Tracker-region defining unit 106 defines a tracker region $R_t$ (see FIG. 33) for detecting a contrast medium.

The MRI apparatus 1 comprises a computer including the processing apparatus 10. The processing apparatus 10 implements the image producing unit 101 to tracker-region defining unit 106, etc. by loading programs stored in the storage section 11. The processing apparatus 10 may implement the image producing unit 101 to tracker-region defining unit 106 by a single processor, or by two or more processors. The programs executed by the processing apparatus 10 may be stored in a single storage section, or separately in a plurality of storage sections. The processing apparatus 10 constitutes the blood vessel detecting apparatus.

Referring back to FIG. 1, the description will be continued. The operating section 12 is operated by an operator to input several kinds of information to the computer 8. The display section 13 displays several kinds of information. The MRI apparatus 1 is configured as described above.

Figure 3:
FIG. 3 is a diagram showing scans performed in the present embodiment.
Figure 4:
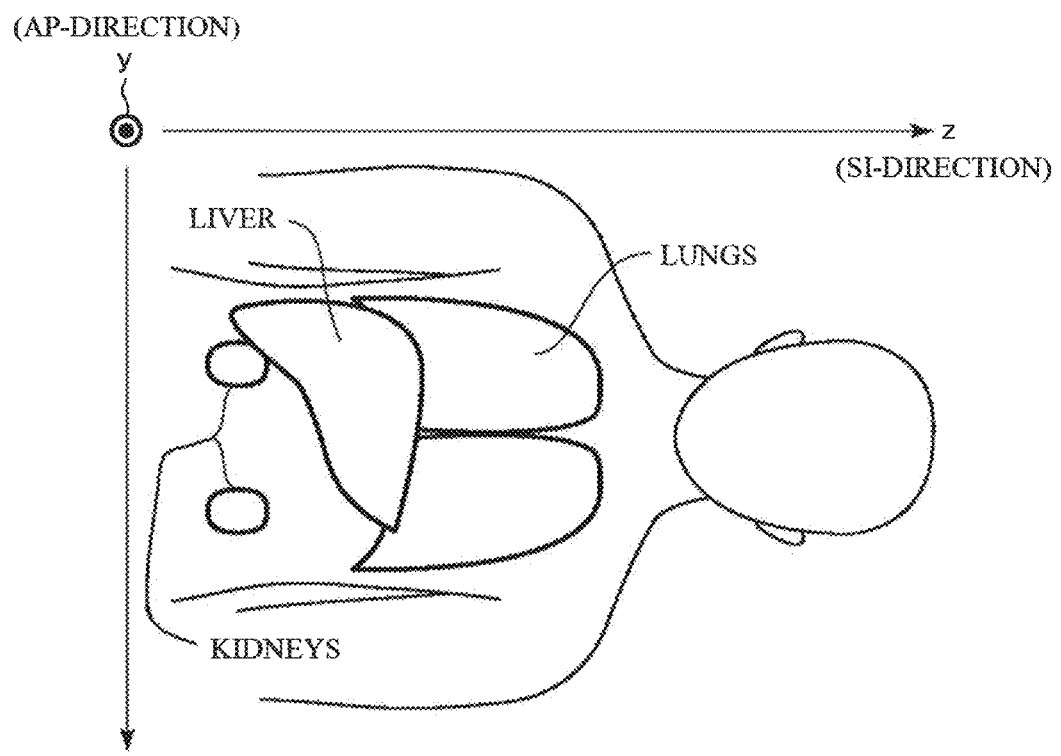
FIG. 4 is a diagram schematically showing a body part to be imaged.
Figure 4:
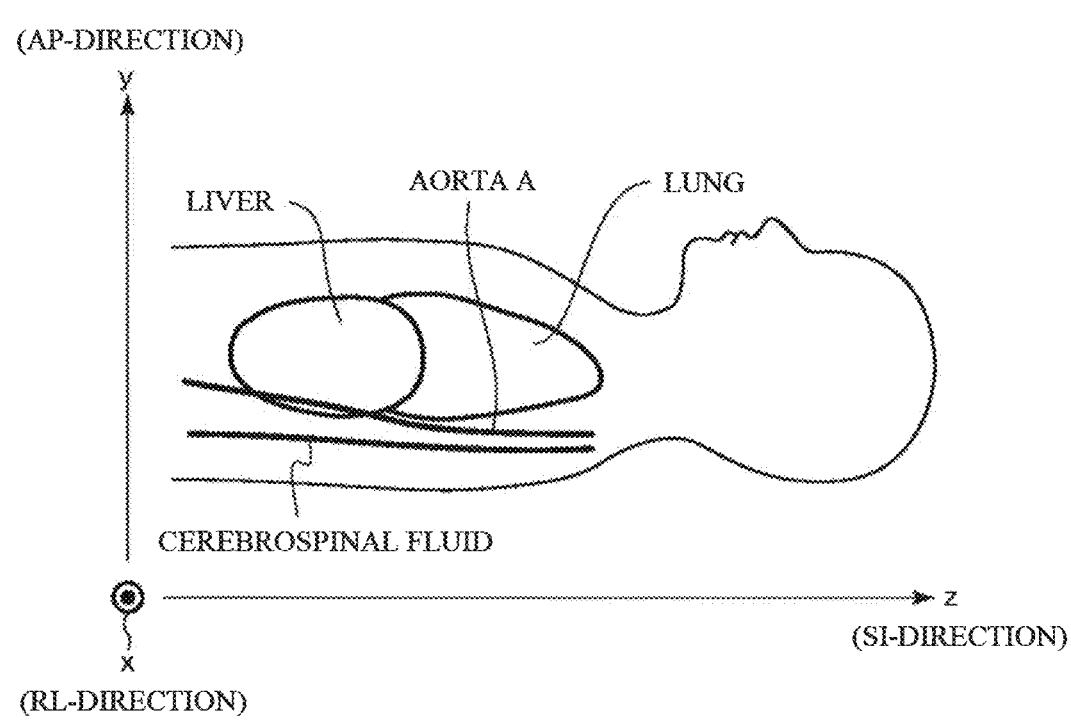

FIG. 3 is a diagram showing scans performed in the present embodiment, and FIG. 4 is a diagram schematically showing a body part to be imaged. In the present embodiment, a localizer scan LS, a main scan MS, etc. are performed. The localizer scan LS is a scan for acquiring an image used in defining slice positions or a tracker region $R_t$ (see FIG. 33). The tracker region $R_t$ is a region defined for detecting a contrast medium flowing through the aorta A. Subsequent to the localizer scan LS, the main scan MS is performed.

In the main scan MS, a contrast medium is injected into the subject, and a sequence for detecting the contrast medium from the tracker region $R_t$ is repetitively performed. Once a predetermined amount of the contrast medium has been injected into the tracker region, an imaging sequence for acquiring an image of a liver is performed. Now an exemplary flow in performing the localizer scan LS and main scan MS will be described below.

Figure 5:
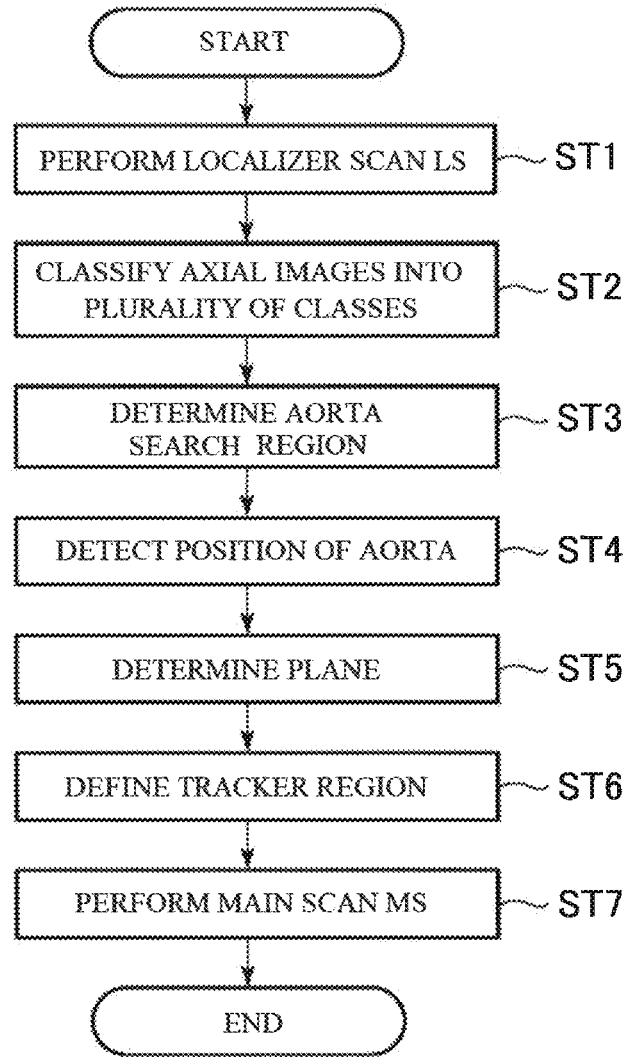
FIG. 5 is a diagram showing an exemplary flow in performing a localizer scan LS and a main scan MS.

FIG. 5 is a diagram showing an exemplary flow in performing the localizer scan LS and main scan MS. At Step ST1, the localizer scan LS (see FIG. 2) is performed.

Figure 6:
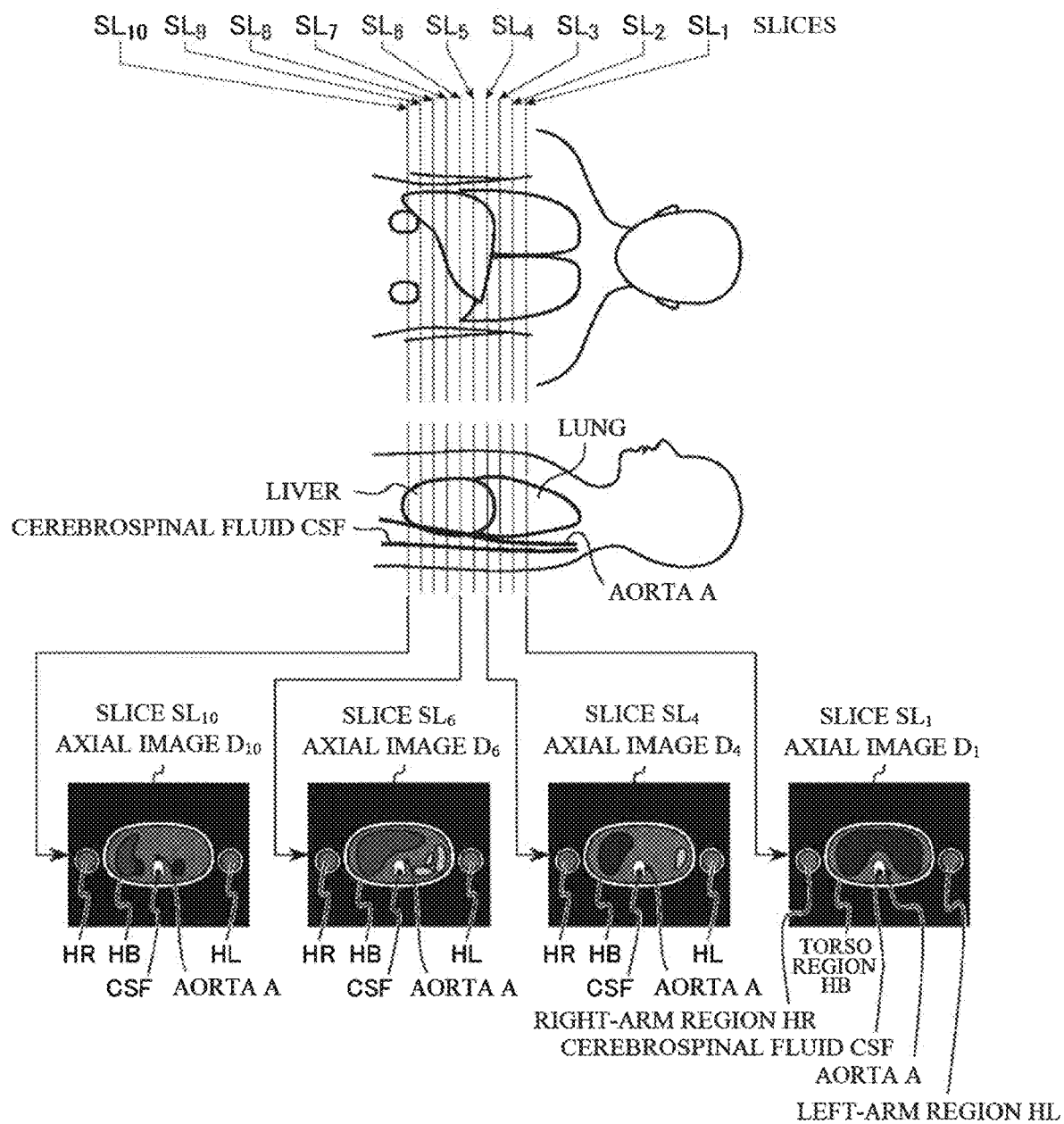
FIG. 6 is a diagram explaining the localizer scan LS.

FIG. 6 is a diagram explaining the localizer scan LS. The localizer scan LS is a scan for acquiring an image of a body part including a liver and organs surrounding the liver in the subject. FIG. 6 shows slices in performing the localizer scan LS. Although the localizer scan LS acquires axial, sagittal, and coronal images, FIG. 6 shows a plurality of slices (ten slices $SL_1$ to $SL_{10}$ here) for acquiring axial images for convenience of explanation.

In performing the localizer scan LS, the control section 6 (see FIG. 1) sends data for an RF pulse in a sequence used in the localizer scan LS to the transmitter 7, and data for a gradient pulse in the sequencer used in the localizer scan LS to the gradient power supply 8. The transmitter 7 supplies electric current to the RF coil 24 based on the data received from the control section 6, while the gradient power supply 8 supplies electric current to the gradient coil 23 based on the data received from the control section 6. Thus, the RF coil 24 applies an RF pulse, while the gradient coil 23 applies a gradient pulse. By performing the localizer scan LS, an MR signal is generated from the body part to be imaged. The MR signal is received by the receive coil 4 (see FIG. 1). The receive coil 4 receives the MR signal and outputs an analog signal containing information on the MR signal. The receiver 9 applies signal processing, such as demodulation/detection, to the signal received from the receive coil 4, and outputs data resulting from the signal processing to the processing apparatus 10.

The image producing unit 101 (see FIG. 2) produces images $D_1$ to $D_{10}$ in the slices $SL_1$ to $SL_{10}$ based on the data collected by the localizer scan LS (which images will be referred to as "axial images" hereinbelow). In the drawing, axial images $D_1$, $D_4$, $D_6$, and $D_{10}$ are schematically shown. Since the slices $SL_1$ to $SL_{10}$ intersect the aorta A, the axial images $D_1$ to $D_{10}$ render cross sections of the aorta A.

An axial image includes three regions. The first one is a region (referred to hereinbelow as "torso region") HB representing a cross section of the torso of the subject, the second is a region (referred to hereinbelow as "left-arm region") HL representing a cross section of the left arm of the subject, and the third is a region (referred to hereinbelow as "right-arm region") HR representing across section of the right arm of the subject. After producing the axial images $D_1$ to $D_{10}$, the flow goes to Step ST2.

At Step ST2, the classifying unit 102 (see FIG. 2) classifies the axial images $D_1$ to $D_{10}$ into a plurality of classes. Now a method of classifying the axial images $D_1$ to $D_{10}$ will be described below. In the following example, a method of classifying the axial images using a Laplacian eigenmaps method will be described.

In the present embodiment, the axial images $D_1$ to $D_{10}$ are classified into four classes as defined as follows:

Class I: axial images having a large cross-sectional area of the lungs;

Class II: axial images intersecting the vicinity of a border between the lungs and liver;

Class III: axial images having a large cross-sectional area of the liver; and

Class IV: axial images intersecting the liver and kidneys.

In the present embodiment, before imaging the subject, a classification map is prepared in advance for classifying each of the axial images $D_1$ to $D_{10}$ according to within which of the four classes I to IV the axial image falls, and the classification of the axial images is achieved using the classification map. Now an exemplary method of creating the classification map will be described below.

Figure 7:
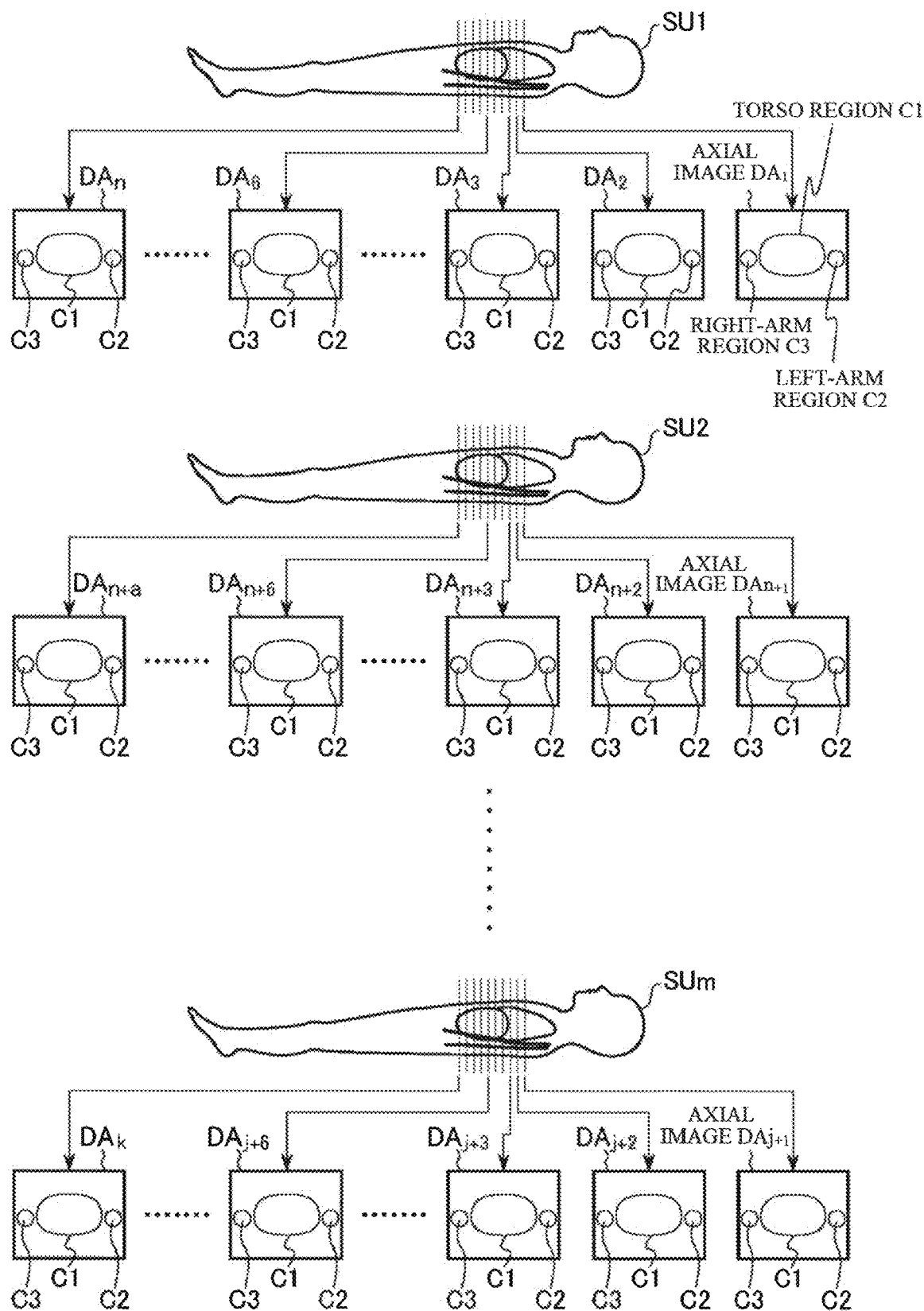
FIG. 7 is a diagram schematically showing axial images $DA_1$ to $DA_n$, $DA_{n+1}$ to $DA_{n+a}$, ..., $DA_{j+1}$ to $DA_k$ for 'm' subjects $SU_1$ to $SU_m$.

FIGS. 7 to 13 are diagrams explaining a method of creating a classification map. First, a plurality of axial images of the abdomen for use to create a classification map are prepared. FIG. 7 shows an example in which a plurality of axial images $DA_1$ to $DA_n$, $DA_{n+1}$ to $DA_{n+a}$, ..., $DA_{j+1}$ to $DA_k$ of the abdomen are prepared from 'm' subjects $SU_1$ to $SU_m$. Each axial image displays a torso region C1, a left-arm region C2, and a right-arm region C3. The present embodiment shows an example in which the 'k' axial images $DA_1$ to $DA_k$ are prepared from the 'm' subjects $SU_1$ to $SU_m$.

Next, a map creator who creates a classification map decides within which of Classes I to IV described above each of the axial images $DA_1$ to $DA_k$ falls. For example, the axial images $DA_1$, $DA_2$, etc. are decided to fall within Class I, while the axial image $DA_k$, etc. are decided to fall within Class IV.

Figure 8:
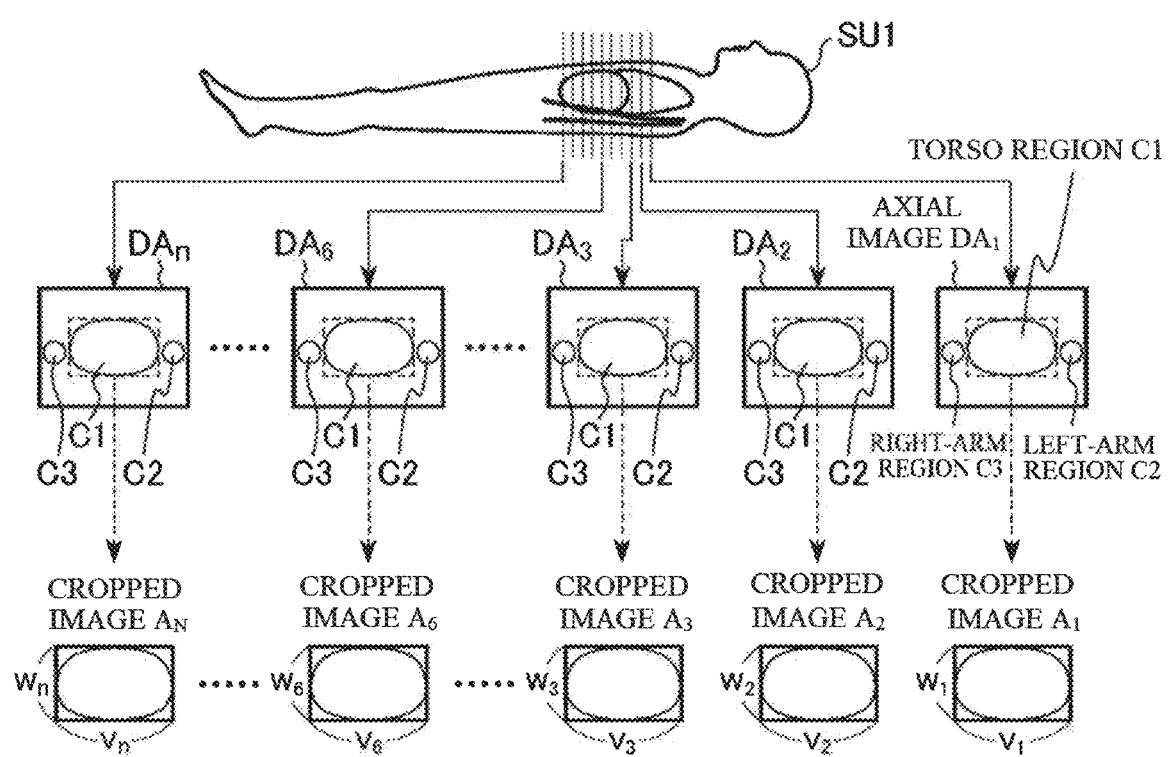
FIG. 8 is a diagram schematically showing images each obtained by cropping an image portion in a rectangular region circumscribing a torso region C1 from an axial image.

Next, an image portion in a rectangular region circumscribing the torso region C1 is clopped from each of the axial images $DA_1$ to $DA_k$. FIG. 8 is a diagram schematically showing images each obtained by cropping an image portion in a rectangular region circumscribing the torso region C1 from the axial image. In FIG. 8, only the subject $SU_1$ is chosen from among the subjects $SU_1$ to $SU_m$ to show images clopped from the axial images for convenience of explanation.

Referring to FIG. 8, images clopped from the axial images $DA_1$ to $DA_n$ are designated by symbols $a_1, a_2, \ldots, a_n$. Moreover, the size of the clopped images $a_1$ to an is represented by the number of pixels: $v_i$ by $w_i$ (i=1 to n). Since the rectangular region circumscribes the torso region C1, the left-arm region C2 and right-arm region C3 may be excluded from the clopped images $a_1$ to $a_n$.

Figure 9:
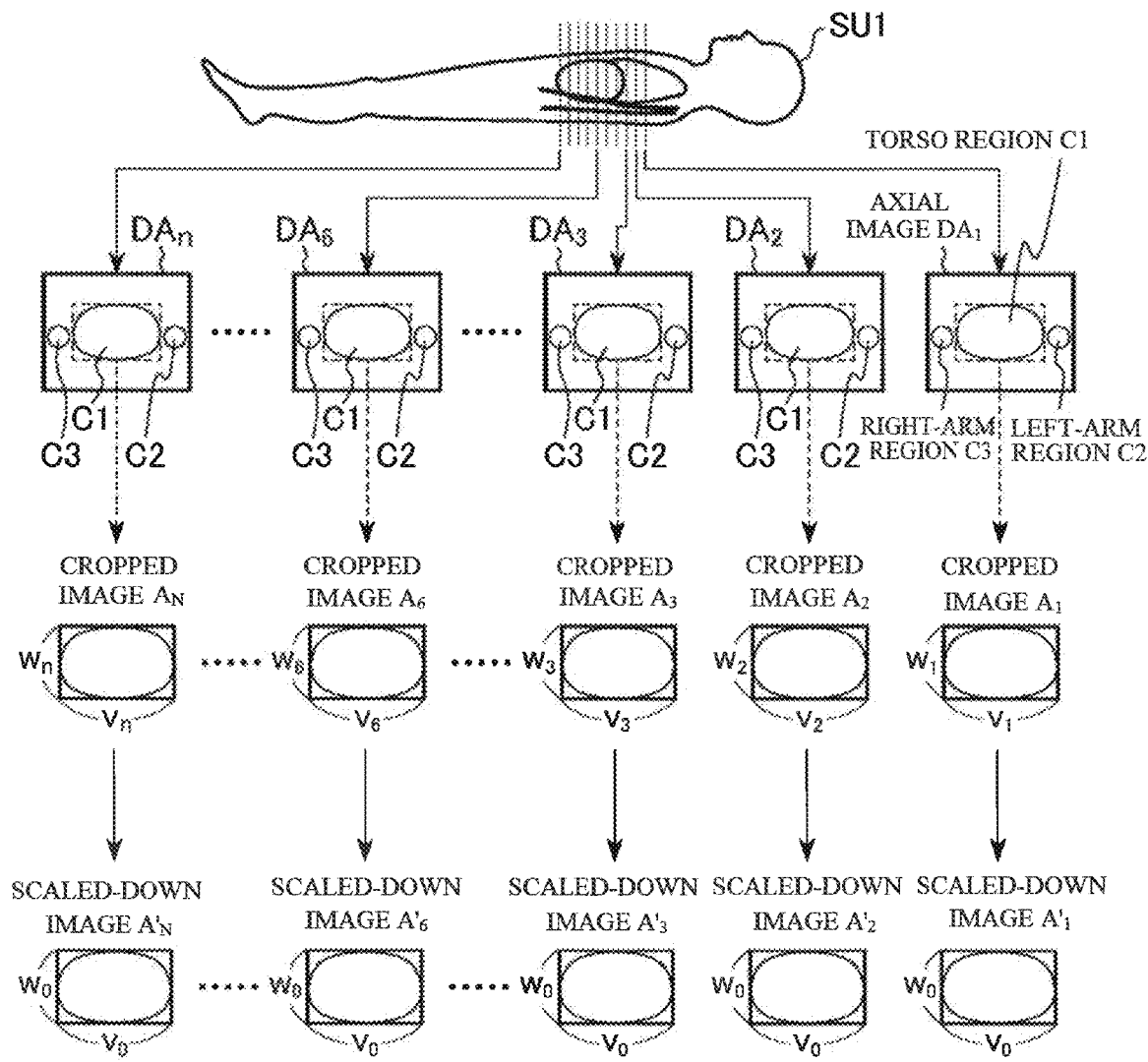
FIG. 9 is a diagram schematically showing images after their resolution is scaled down.

After cropping the image portion of the torso from the axial images $DA_1$ to $DA_n$, the resolution of the clopped images $a_1$ to $a_n$ is scaled down. FIG. 9 is a diagram schematically showing images after their resolution is scaled down. The scaled-down images are designated by symbols $a_1', a_2', \ldots, a_n'$. The scaled-down images $a_1'$ to $a_n'$ are scaled down to a resolution ($v_0$ by $w_0$) of the same size. For example, $v_0$=44 and $w_0$=22. By thus scaling down the images, images $a_1'$ to $a_n'$ of the same resolution may be produced.

Figure 10:
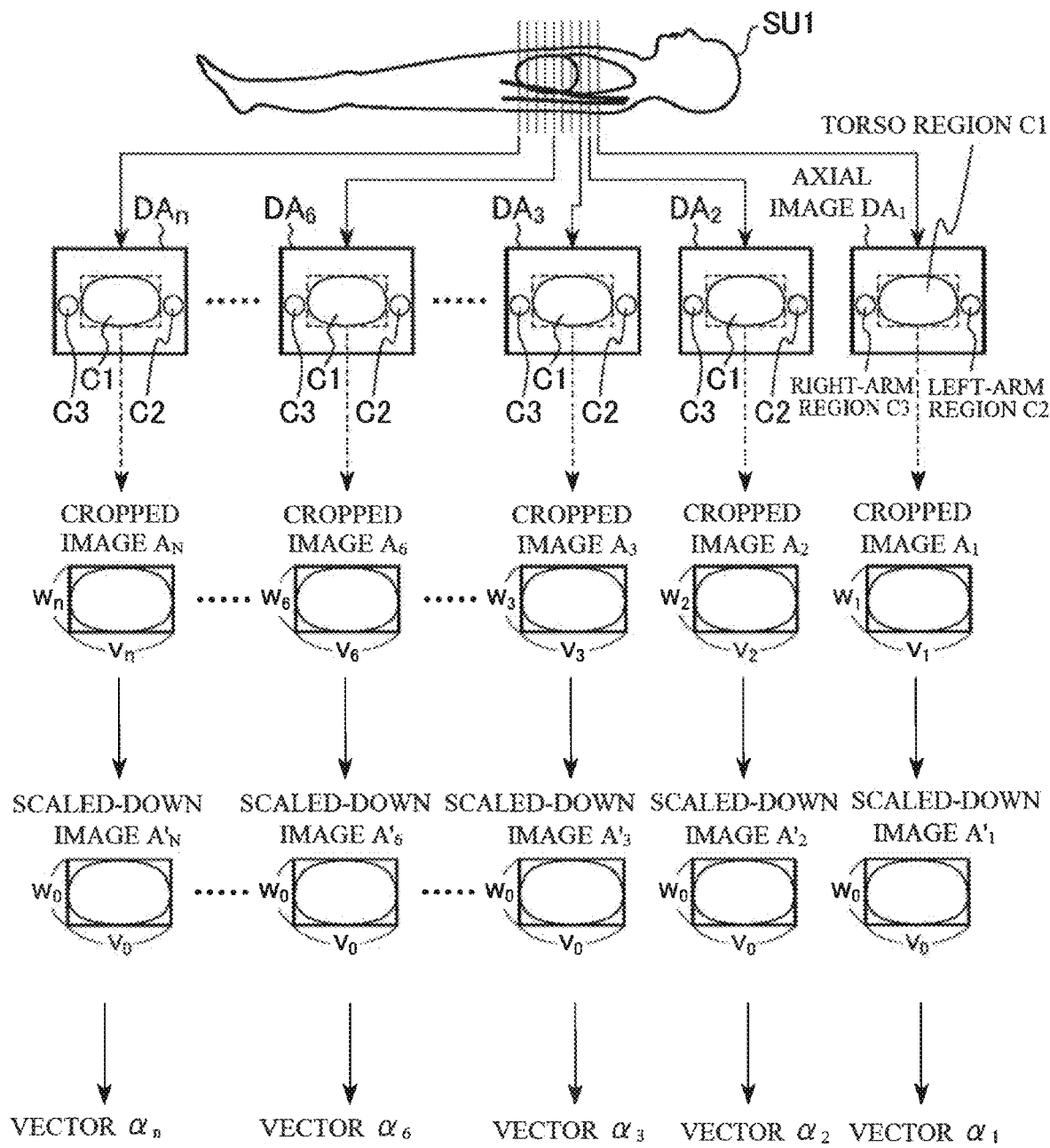
FIG. 10 is a diagram showing a vector determined for each of the scaled-down images $a_1'$ to $a_n'$.

Next, a vector for each of the scaled-down images $a_1'$ to $a_n'$ is determined. FIG. 10 is a diagram showing a vector determined for each of the scaled-down images $a_1'$ to $a_n'$.

First, let us consider a vector $\alpha_1$ for an i-th image $a_1'$ of the scaled-down images $a_1'$ to $a_n'$. The vector $\alpha_1$ is a vector defined so that its elements are pixel values of pixels in the image $a_i'$. Representing the number of pixels of the image $a_i'$ as t (=$v_0$ by $w_0$), the vector $\alpha_i$ may be expressed by the following equation:

$$\alpha_i=(\alpha_{i1}, \alpha_{i2}, \alpha_{i3}, \alpha_{i4}, \alpha_{i5}, \ldots, \alpha_{it}) \quad (1)$$

where $\alpha_{i1}, \alpha_{i2}, \alpha_{i3}, \alpha_{i4}, \alpha_{i5}, \ldots, \alpha_{it}$ denote pixel values of pixels in the image $a_1'$, so that the vector $\alpha_i$ is expressed by the vector having 't' elements.

Therefore, a vector when i=1, for example, that is, a vector $\alpha_1$ for the image $a_1'$, may be expressed by the following equation:

$$\alpha_1=(\alpha_{11}, \alpha_{12}, \alpha_{13}, \alpha_{14}, \alpha_{15}, \ldots, \alpha_{1t}) \quad (2)$$

Referring to FIG. 10, representative vectors $\alpha_1$, $\alpha_2$, $\alpha_3$, $\alpha_6$, and $\alpha_n$ when i=1, 2, 3, 6, and n are shown.

Figure 11:
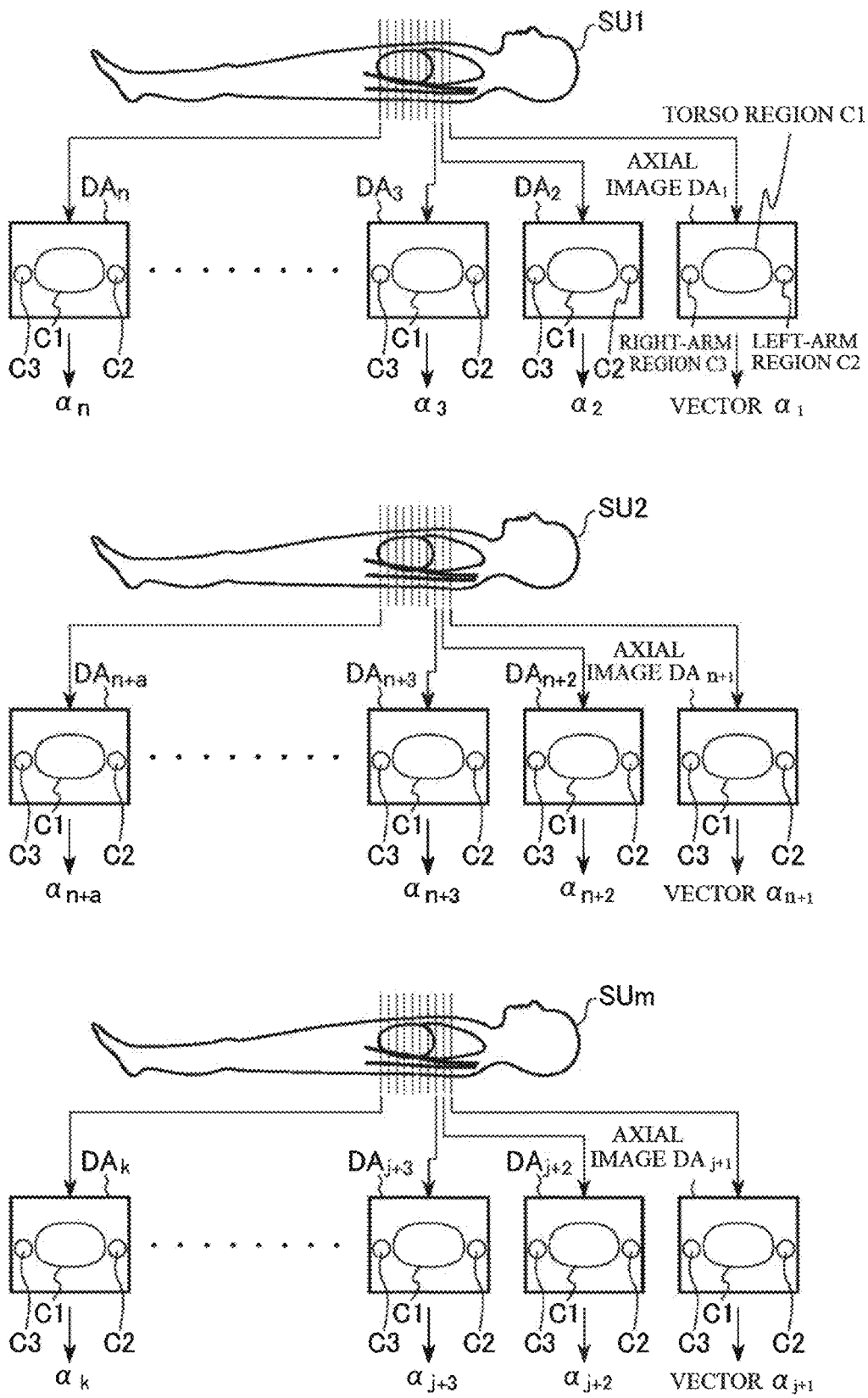
FIG. 11 is a diagram showing a vector $\alpha_i$ obtained for each axial image for the subjects $SU_1$ to $SU_m$.

While FIGS. 8 to 10 explain an example in which the vectors $\alpha_1$ to $\alpha_n$ for the axial images $DA_1$ to $DA_n$ for the subject $SU_1$ are determined, the vector $\alpha_i$ may be determined for axial images for the other subjects $SU_2$ to $SU_m$ as well according to the method described above. FIG. 11 shows vectors $\alpha_i$ obtained for the subjects $SU_1$ to $SU_m$ on an axial image-by-axial image basis. In the present embodiment, 'k' axial images $DA_1$ to $DA_k$ are prepared from the subjects $SU_1$ to $SU_m$, so that 'k' vectors $\alpha_1$ to $\alpha_k$ are obtained.

After determining these vectors $\alpha_1$ to $\alpha_k$, an adjacency matrix MA is determined. FIG. 12 schematically shows the adjacency matrix MA. Each element in the adjacency matrix MA represents a distance $d_{ij}$ between two vectors.

After determining the adjacency matrix MA, it is weighted by a heat kernel according to the distance $d_{ij}$ to thereby obtain a matrix W. Then, a diagonal matrix D whose diagonal elements are respective sums of columns in the matrix W is determined, and a Laplacian matrix is obtained based on the matrices W and D.

Figure 13:
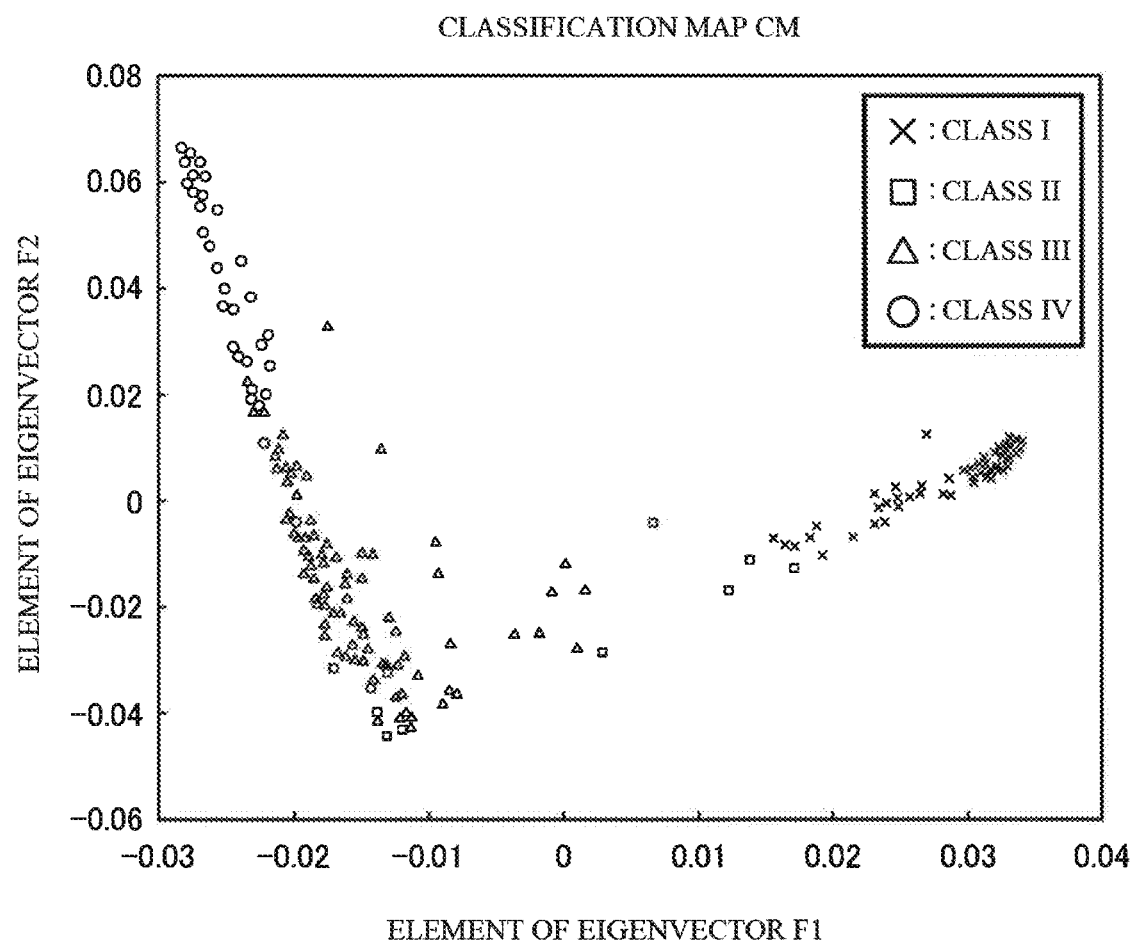
FIG. 13 is a diagram showing a classification map CM.

After obtaining the Laplacian matrix, an eigenproblem for the Laplacian matrix is solved to obtain 'k' eigenvectors. After obtaining the 'k' eigenvectors, an eigenvector F1 having a smallest eigenvalue, and an eigenvector F2 having a second smallest eigenvalue are identified from among the 'k' eigenvectors. Thus, the two eigenvectors F1 and F2 may be used to obtain a map representing a relationship among the axial images $DA_1$ to $DA_k$ (see FIG. 7) for the subjects $SU_1$ to $SU_m$. FIG. 13 schematically shows an example of a resulting map. A horizontal axis of the map CM represents an element of the eigenvector F1, while a vertical axis represents an element of the eigenvector F2. Positions of the axial images $DA_1$ to $DA_k$ in the map CM may be determined by a coordinate point (f1, f2) (f1: the element of the eigenvector F1, and f2: the element of the eigenvector F2). In FIG. 13, points representing the positions of the axial images $DA_1$ to $DA_k$ are represented using four marks (a cross, a hollow square, a hollow triangle, and a hollow circle) for convenience of explanation. The cross indicates a point representing the position of an axial image falling within Class I (an axial image having a large cross-sectional area of the lungs). The hollow square indicates a point representing the position of an axial image falling within Class II (an axial image intersecting the vicinity of a border between the lungs and liver). The hollow triangle indicates a point representing the position of an axial image falling within Class III (an axial image having a large cross-sectional area of the liver). The hollow circle indicates a point representing the position of an axial image falling within Class IV (an axial image intersecting the liver and kidneys).

In the present embodiment, the map CM shown in FIG. 13 is used as a classification map for classifying the axial images $D_1$ to $D_{10}$ (see FIG. 6) obtained in the localizer scan LS. The classification map CM is stored in the storage section 11 (see FIG. 1).

At Step ST2, the classifying unit 102 classifies the axial images $D_1$ to $D_{10}$ obtained in the localizer scan LS into the plurality of classes I to IV based on the classification map CM stored in the storage section 11. Now a procedure of classifying the axial images $D_1$ to $D_{10}$ into the plurality of classes I to IV based on the classification map CM will be described referring to FIG. 14.

Figure 14:
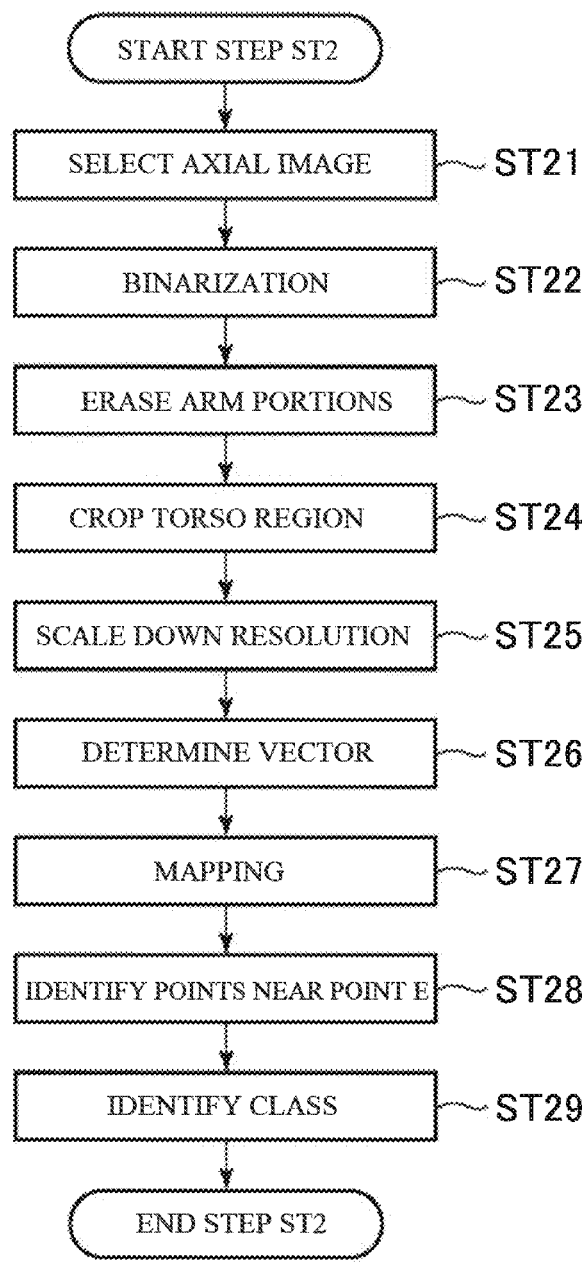
FIG. 14 is a diagram showing an exemplary flow of Step ST2.

FIG. 14 is a diagram showing an exemplary flow of Step ST2. Step ST2 has Steps ST21 to ST29. Now Steps ST21 to ST29 will be described one by one.

Figure 15:
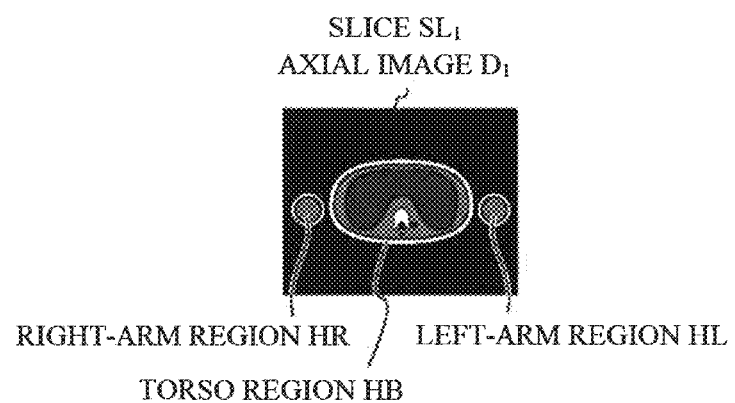
FIG. 15 is a diagram schematically showing an axial image $D_1$ in a slice $SL_1$.

At Step ST21, the classifying unit 102 selects one axial image from among the axial images $D_1$ to $D_{10}$ in the slices $SL_1$ to $SL_{10}$. Assume here that the axial image $D_1$ in the slice $SL_1$ intersecting the lungs is selected. FIG. 15 schematically shows the selected axial image $D_1$ in the slice $SL_1$. In the axial image $D_1$, a torso region HB in the subject, and in addition, a left-arm region HL and a right-arm region HR are rendered. After selecting the axial image $D_1$ in the slice $SL_1$, the flow goes to Step ST22.

Figure 16:
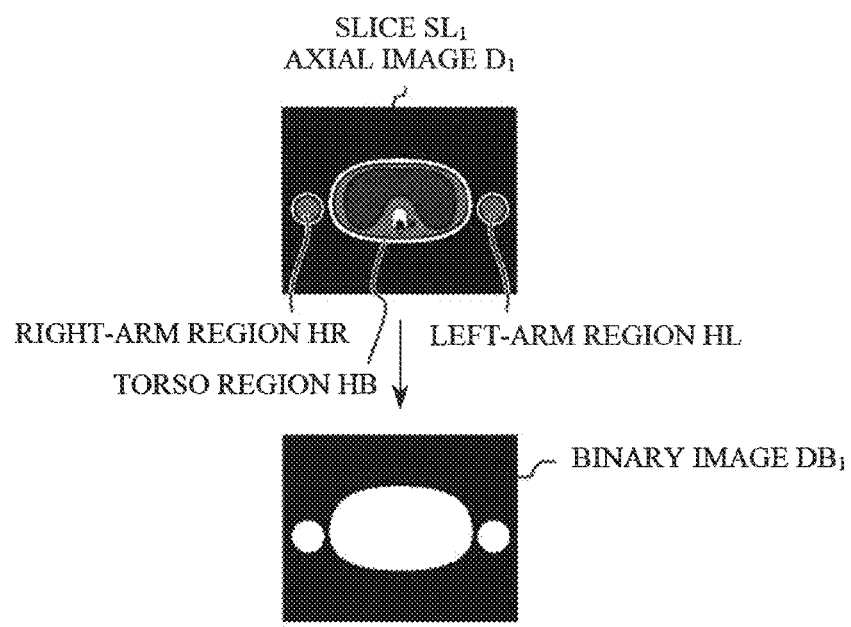
FIG. 16 is a diagram schematically showing a binary image $DB_1$ obtained by binarizing the axial image $D_1$ in the slice $SL_1$.

At Step ST22, the classifying unit 102 binarizes the axial image $D_1$ in the slice $SL_1$. FIG. 16 schematically shows a binary image $DB_1$ obtained by binarizing the axial image $D_1$ in the slice $SL_1$. The classifying unit 102 executes binarization processing so that the torso region HB, left-arm region HL, and right-arm region HR are rendered with a logical value of one, while regions outside of the body are rendered with a logical value of zero. This provides the binary image $DB_1$ in which regions inside of the body are rendered with a logical value of one and regions outside of the body are rendered with a logical value of zero. A method of binarization that may be employed is, for example, a region growing method as described in "Med. Imag. Tech., Vol. 31, No. 2, March 2013." After applying binarization, the flow goes to Step ST23.

At Step ST23, the classifying unit 102 executes processing of erasing arm portions from the binary image $DB_1$.

Figure 17:
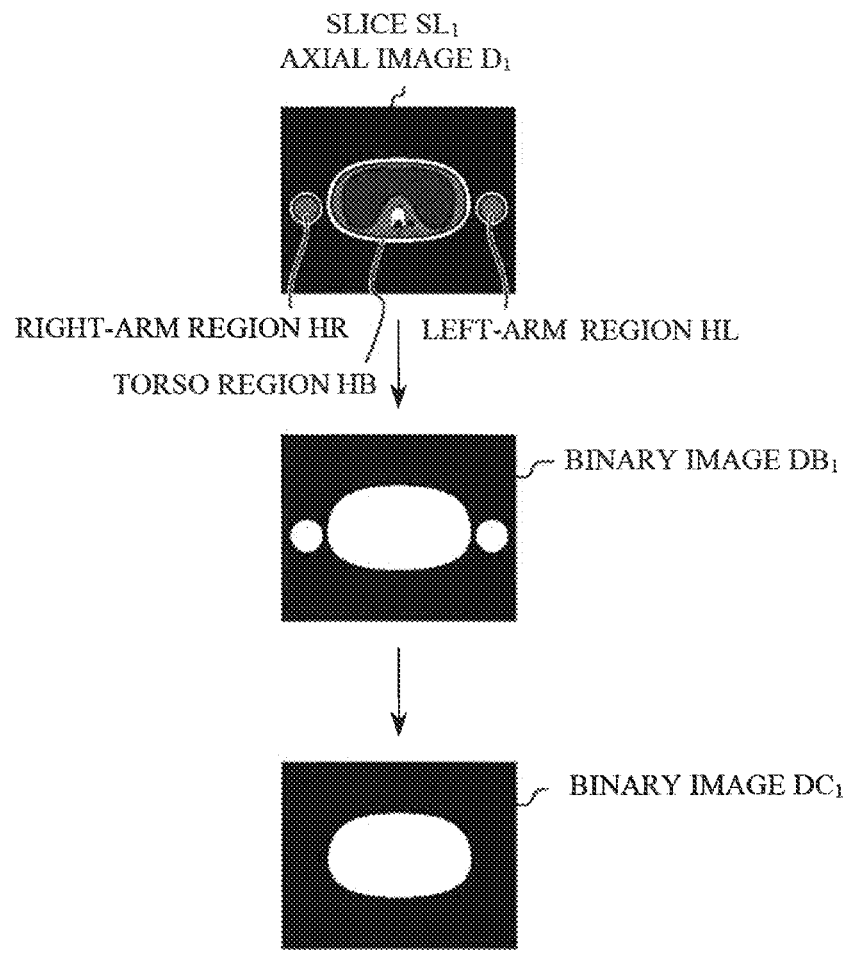
FIG. 17 is a diagram schematically showing a binary image $DC_1$ in which arm portions are erased.

FIG. 17 is a diagram schematically showing a binary image $DC_1$ in which the arm portions are erased. At Step ST23, image processing for erasing the left-arm and right-arm regions from the binary image $DB_1$ is executed. This provides the binary image $DC_1$ in which the arm portions are erased. A method of erasing arm portions that may be employed is, for example, a method executing erosion processing, region growing processing, and dilation processing, as described in "Med. Imag. Tech., Vol. 31, No. 2, March 2013." After obtaining the binary image $DC_1$ in which the arm portions are erased, the flow goes to Step ST24.

Figure 18:
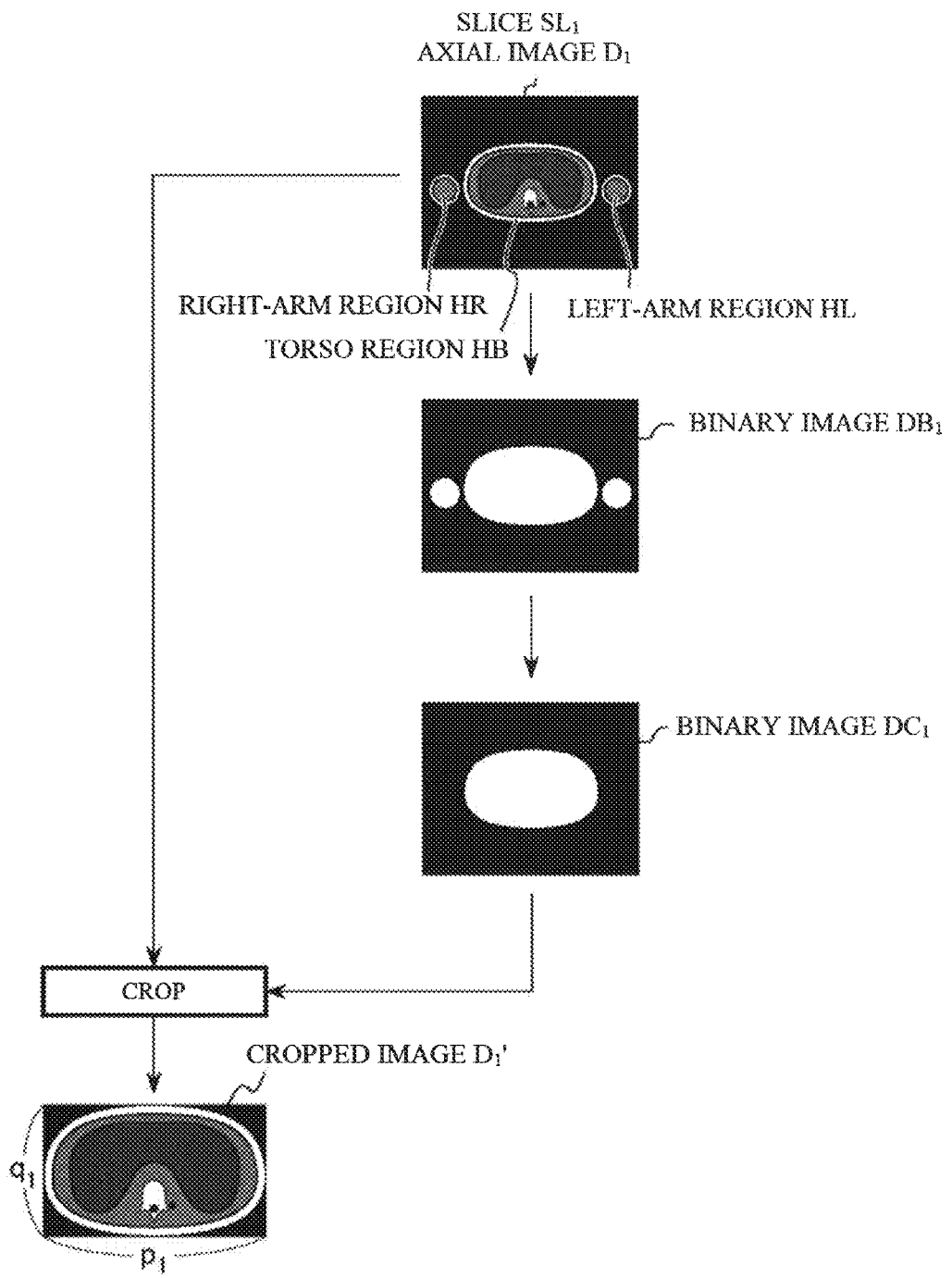
FIG. 18 is a diagram schematically showing an image obtained by cropping an image portion in a rectangular region circumscribing a torso region HB from the axial image $D_1$.

At Step ST24, the classifying unit 102 clops an image portion in a rectangular region circumscribing the torso region HB from the axial image $D_1$ based on the binary image $DC_1$ obtained at Step ST23. FIG. 18 schematically shows an image obtained by cropping the image portion in a rectangular region circumscribing the torso region HB from the axial image $D_1$. Since in the binary image $DC_1$, the torso region has a logical value of one and regions outside of the torso are assigned with a logical value of zero, the torso region HB within the axial image $D_1$ may be identified by using the binary image $DC_1$. Thus, a rectangular region circumscribing the torso region HB may be clopped from the axial image $D_1$. In FIG. 18, the image clopped from the axial image $D_1$ is designated by symbol $D_1'$. Moreover, the size of the clopped image $D_1'$ is represented by a number of pixels of $p_1$ by $q_1$. Since the rectangular region circumscribes the torso region HB, the left-arm region HL and right-arm region HR may be excluded from the rectangular region. After cropping the image portion of the torso region from the axial image $D_1$, the flow goes to Step ST25.

Figure 19:
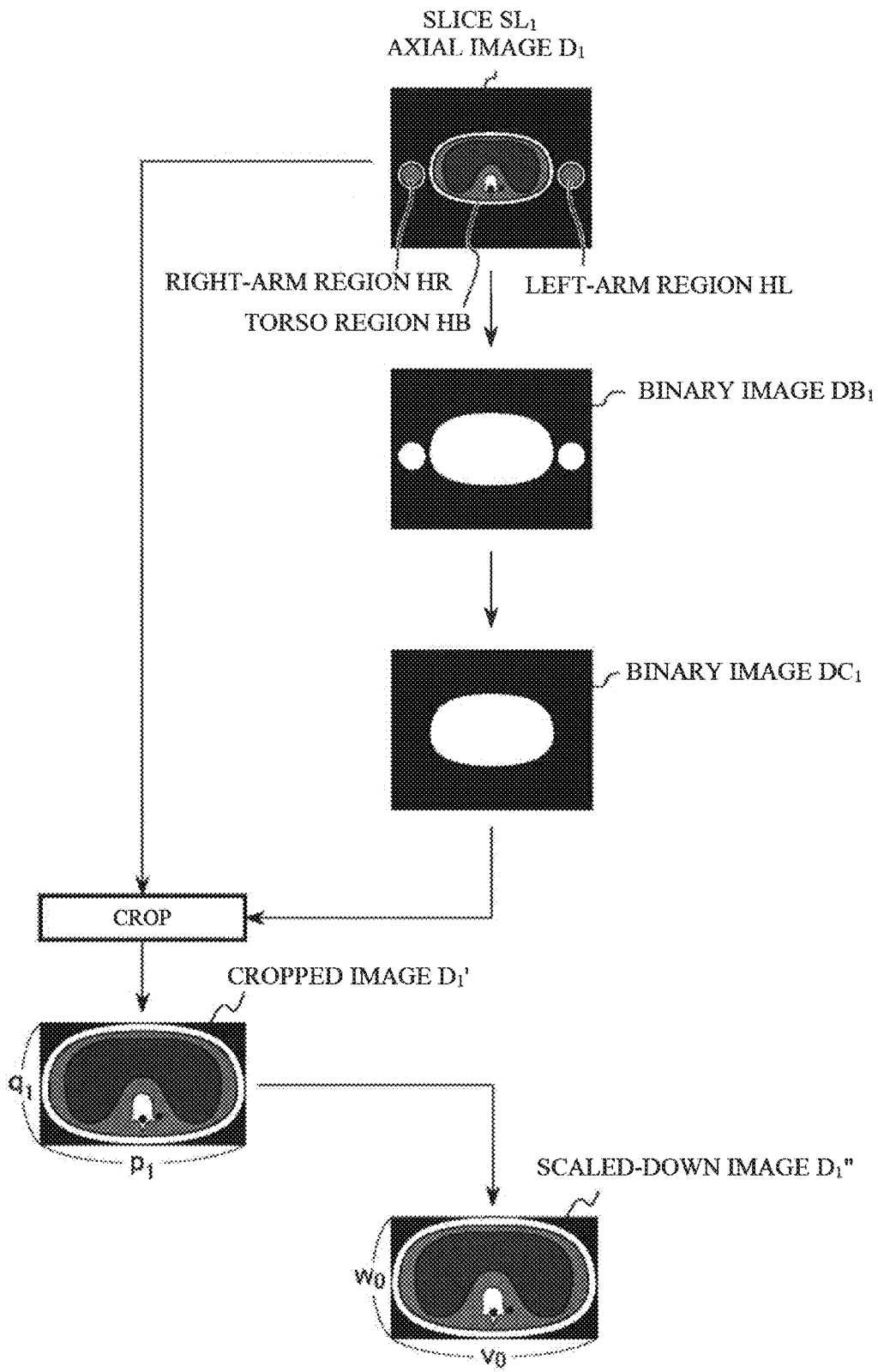
FIG. 19 is a diagram schematically showing an image $D_1''$ after its resolution is scaled down.

At Step ST25, the classifying unit 102 scales down the resolution of the clopped image $D_1'$. FIG. 19 is a diagram schematically showing an image $D_1''$ after its resolution is scaled down. The scaled-down image $D_1''$ has been scaled down to a resolution ($v_0$ by $w_0$) of the same size as the images $a_1'$ to $a_n'$ (see FIG. 10) used in creating the classification map CM. After scaling down the resolution, the flow goes to Step ST26.

Figure 20:
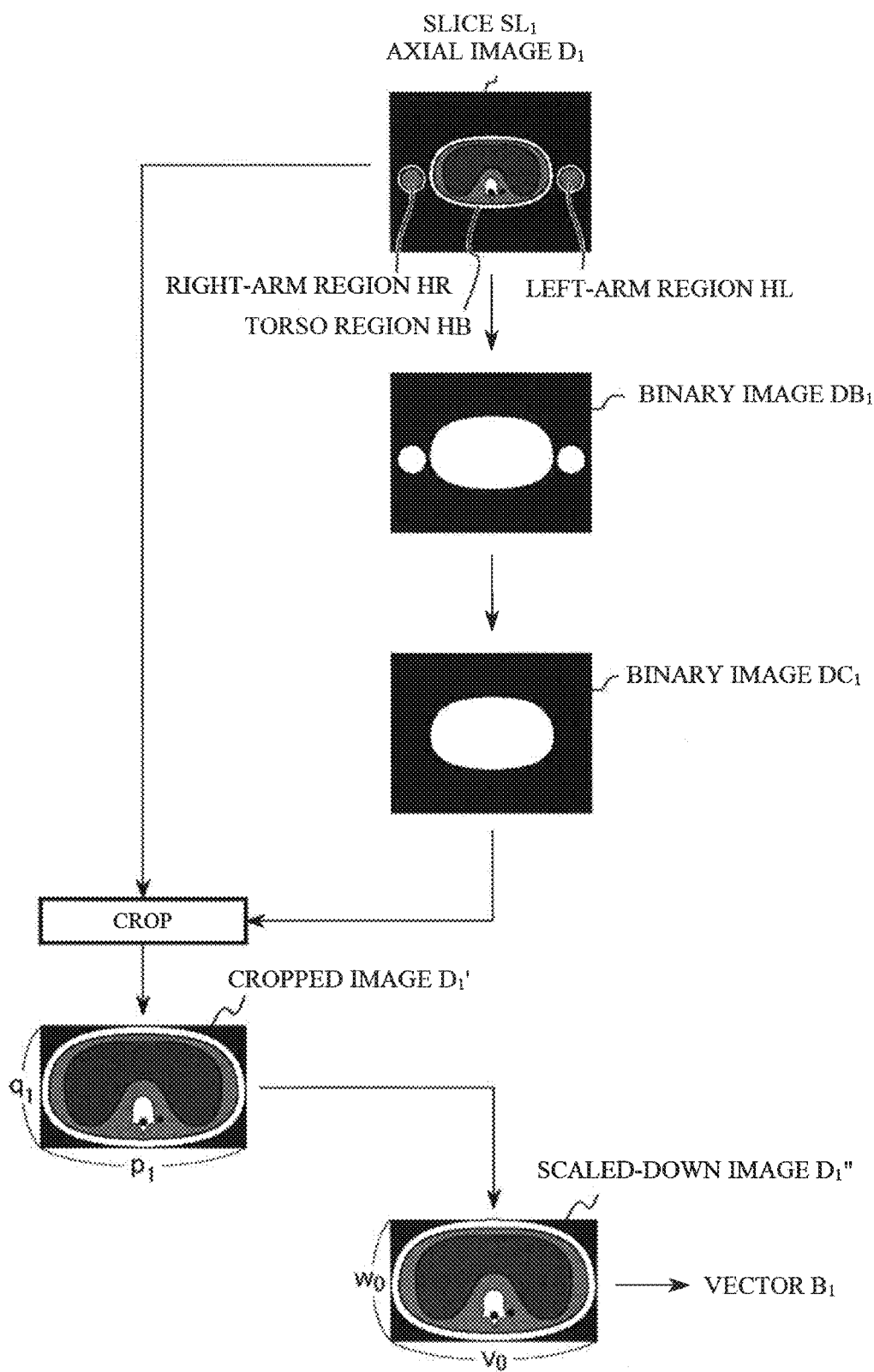
FIG. 20 is a diagram showing a vector $\beta_1$ determined for the scaled-down image $D_1''$.

At Step ST26, the classifying unit 102 determines a vector for the scaled-down image $D_1''$ (see FIG. 20).

FIG. 20 is a diagram showing a vector $\beta_1$ determined for the scaled-down image $D_1''$. The vector $\beta_1$ is a vector defined so that its elements are pixel values of pixels in the scaled-down image $D_1''$. The vector $\beta_1$ may be expressed by the following equation:

$$\beta = (\beta_{11}, \beta_{12}, \beta_{13}, \beta_{14}, \beta_{15}, \ldots, \beta_{1t}) \quad (3)$$

where $\beta_{11}, \beta_{12}, \beta_{13}, \beta_{14}, \beta_{15}, \ldots, \beta_{1t}$ denote pixel values of pixels in the scaled-down image $D_1''$. After determining the vector $\beta_1$, the flow goes to Step ST27.

Figure 21:
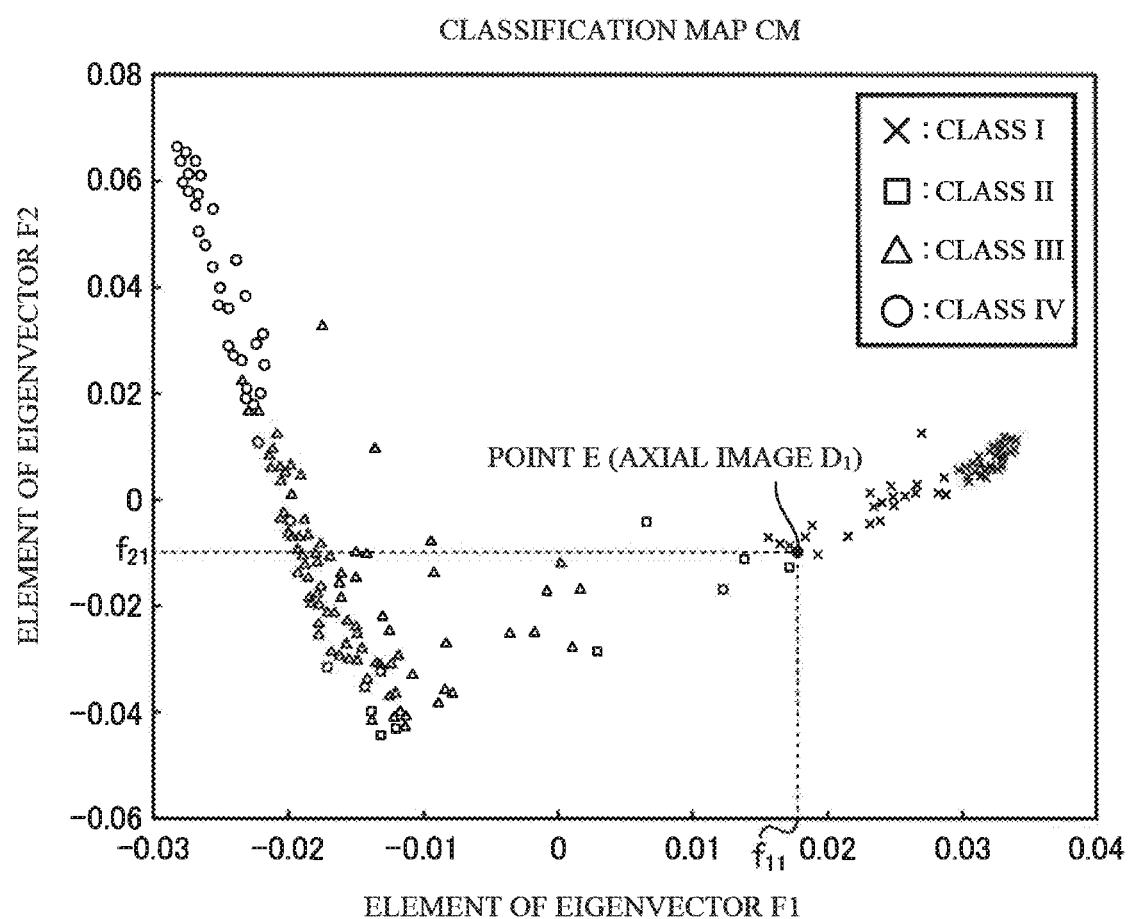
FIG. 21 is a diagram showing a point E projected onto the classification map CM.

At Step ST27, the classifying unit 102 determines a distance between each of the 'k' vectors $\alpha_1$ to $\alpha_k$ (see FIG. 11) used to create the classification map CM and the vector $\beta_1$ for the axial image $D_1$. The distance is then weighted with a heat kernel according to the distance value to determine a matrix Y. Next, the two eigenvectors F1 and F2 identified in creating the classification map CM are used to project the matrix Y onto the classification map CM (see FIG. 13). FIG. 21 shows a point E representing the matrix Y projected onto the classification map CM. In FIG. 21, the point E lies at coordinates (f11, f21). In this way, the point E corresponding to the axial image $D_1$ is mapped onto the classification map CM. After the mapping, the flow goes to Step ST28.

At Step ST28, the classifying unit 102 identifies N points from among a plurality of points defined on the classification map CM in an ascending order of distance to the point E corresponding to the axial image $D_1$.

Figure 22:
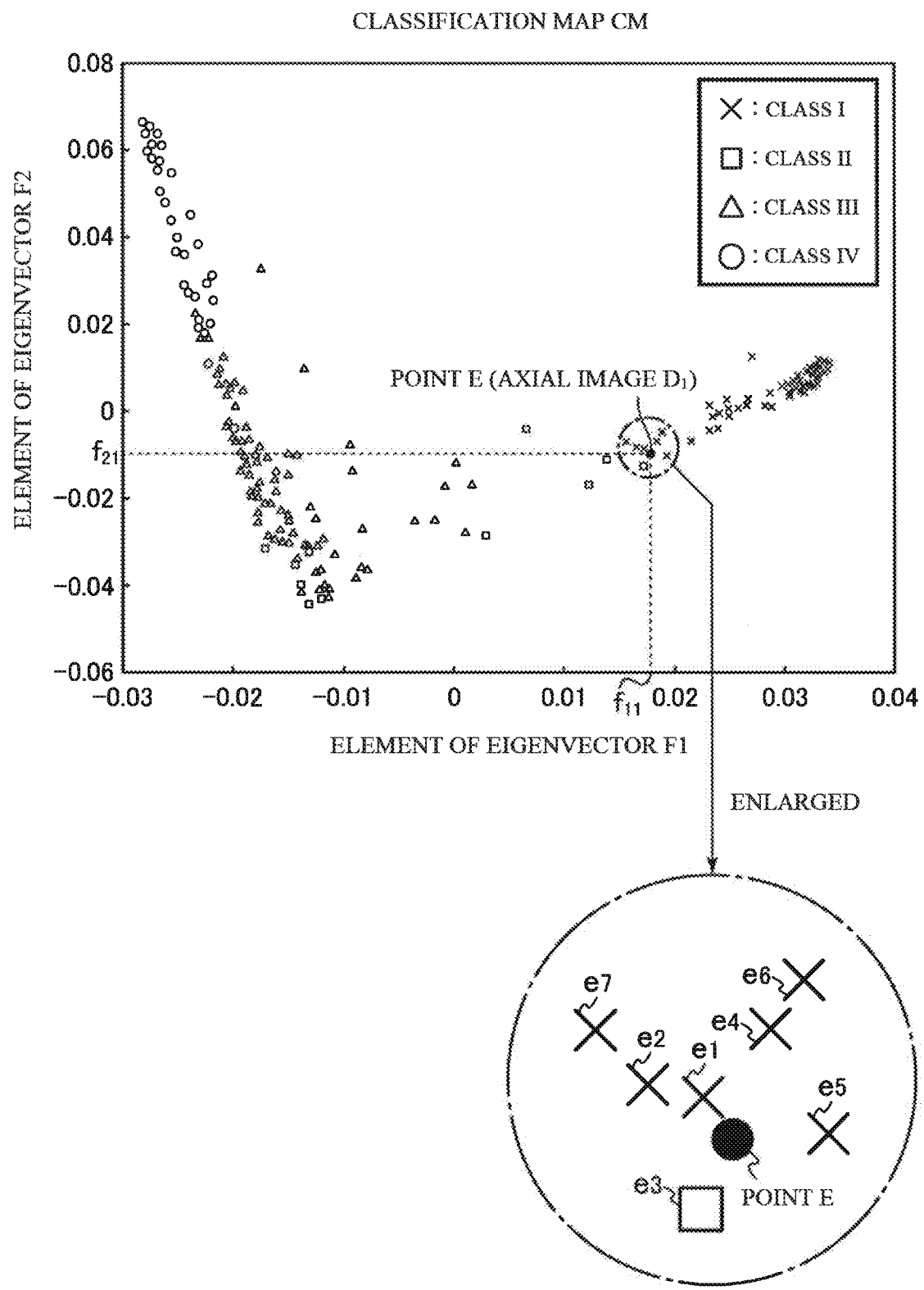
FIG. 22 is a diagram explaining a method of identifying N points.

FIG. 22 is a diagram explaining a method of identifying N points. FIG. 22 shows the vicinity of the point E mapped onto the classification map CM in an enlarged view.

The classifying unit 102 calculates a distance between each of the plurality of points defined on the classification map CM and the point E, and identifies N points in an ascending order of distance. Thus, N points may be identified in an ascending order of distance to the point E. Assume here that N=7. Therefore, seven points e1, e2, e3, e4, e5, e6, and e7 are identified in an ascending order of distance to the point E. After identifying the seven points e1 to e7, the flow goes to Step ST29.

At Step ST29, the classifying unit 102 first identifies within which of the four classes I to IV each of the seven points e1 to e7 falls. Here, six points (e1, e2, e4, e5, e6, and e7) of the seven points e1 to e7 are identified as falling within Class I, and one point (e3) as falling within Class II.

After identifying within which class each point falls, the classifying unit 102 determines how many of the seven points fall within each class, and identifies a class having a largest number of the points falling there. Since six of the seven points e1 to e7 fall within Class I here, Class I is identified. Therefore, the axial image $D_1$ is decided to fall within Class I of the four classes I to IV, so that the axial image $D_1$ is classified into Class I.

While the preceding description is addressed to classification of the axial image $D_1$, the other axial images $D_2$ to $D_{10}$ are also classified according to the flow from Step ST21 to Step ST29. Since information on each of Classes I to IV is reflected in the classification map CM, which portion of the imaged body part each of the axial images $D_1$ to $D_{10}$ represents may be identified by using the classification map CM. Thus, the axial images $D_1$ to $D_{10}$ may be classified into four classes.

Figure 23:
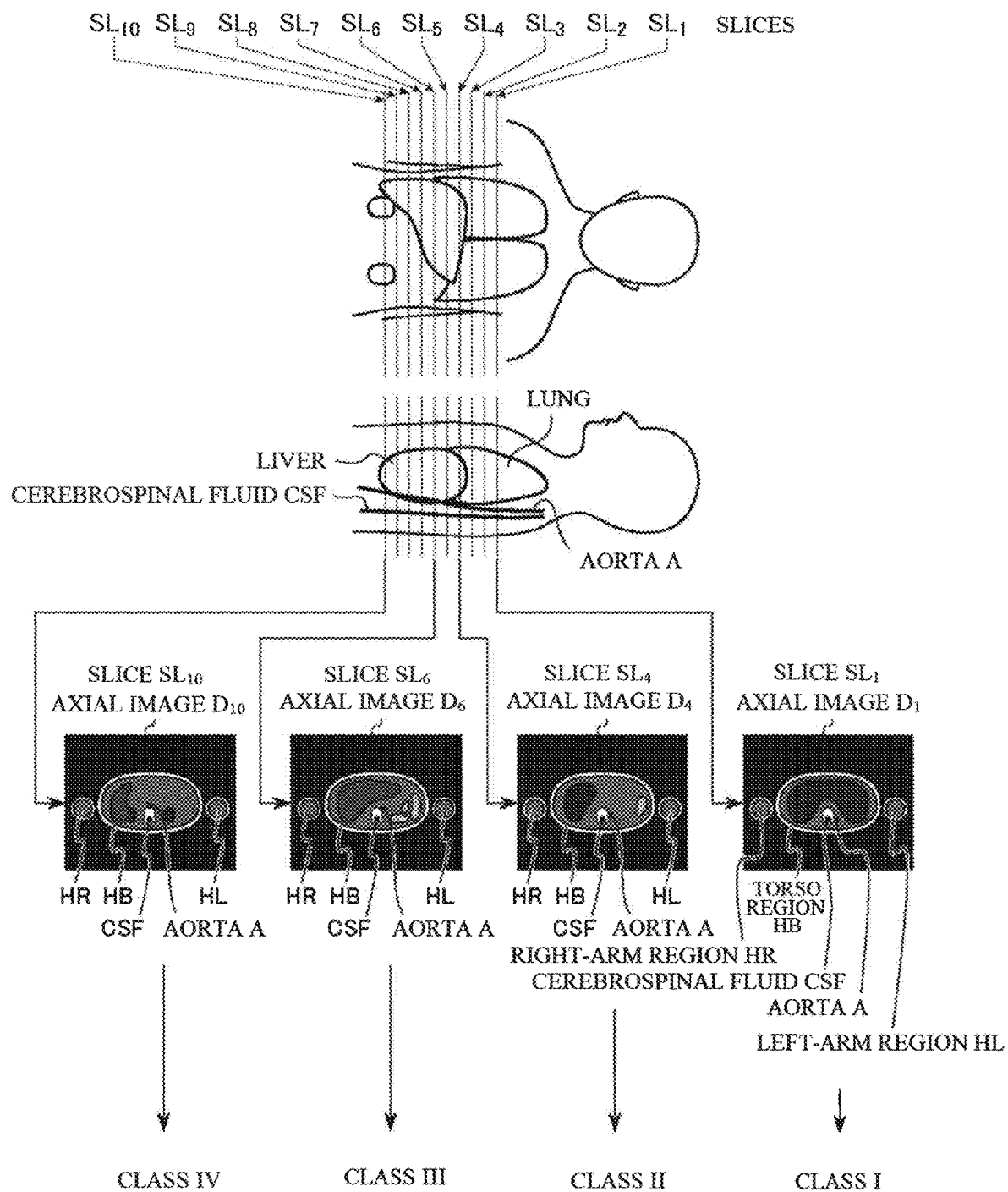
FIG. 23 is a diagram showing within which class each of the axial images $D_1$ to $D_{10}$ falls.

FIG. 23 is a diagram showing within which class each of the axial images $D_1$ to $D_{10}$ falls. FIG. 23 shows within which class four representative axial images $D_1$, $D_4$, $D_6$, and $D_{10}$ of the axial images $D_1$ to $D_{10}$ fall. The axial image $D_1$ is classified into Class I, the axial image $D_4$ into Class II, the axial image $D_6$ into Class III, and the axial image $D_{10}$ into Class IV. After classifying the axial images $D_1$ to $D_{10}$, the flow goes to Step ST3.

At Step ST3, the search-region defining unit 103 (see FIG. 2) defines an aorta search region for each of the axial images $D_1$ to $D_{10}$. Now a method of defining the aorta search region will be described below.

In the present embodiment, a probability distribution model expressing the probability of presence of the aorta for each of Classes I to IV is stored in the storage section 11.

Figure 24:
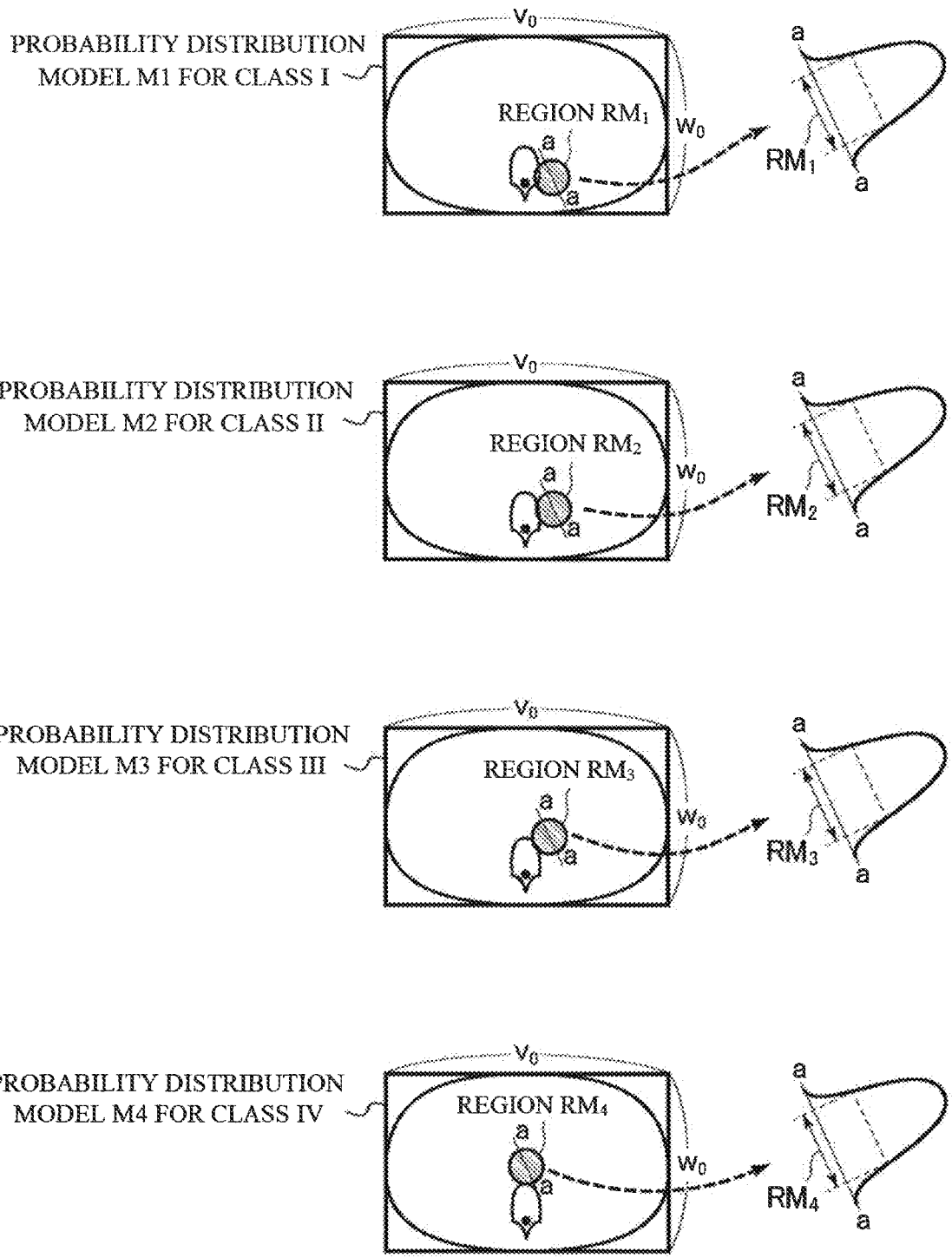
FIG. 24 is a diagram explaining a probability distribution model.

FIG. 24 is a diagram explaining the probability distribution model. The storage section 11 stores therein four probability distribution models M1 to M4.

The probability distribution model M1 represents the probability of presence of the aorta in Class I. The probability of presence of the aorta in Class I may be determined based on the position of the aorta appearing in axial images (for example, axial images $DA_1$, $DA_{n+1}$, $DA_{j+1}$) having a large cross-sectional area of the lungs among the plurality of axial images $DA_1$ to $DA_k$ (see FIG. 7) used to create the classification map CM. A region RM1 in the probability distribution model M1 represents a region having a high probability of presence of the aorta. Referring to an a-a cross section of the probability distribution model M1, it is shown that the probability of presence of the aorta increases from an outer periphery of the region RM1 toward the inside thereof.

The probability distribution model M2 represents the probability of presence of the aorta in Class II. The probability of presence of the aorta in Class II may be determined based on the position of the aorta appearing in axial images (for example, axial images $DA_3$, $DA_{n+3}$, $DA_{j+3}$) intersecting the vicinity of a border between the lungs and liver among the plurality of axial images $DA_1$ to $DA_k$ (see FIG. 7) used to create the classification map CM. A region RM2 in the probability distribution model M2 represents a region having a high probability of presence of the aorta. Referring to an a-a cross section of the probability distribution model M2, it is shown that the probability of presence of the aorta increases from an outer periphery of the region RM2 toward the inside thereof.

The probability distribution model M3 represents the probability of presence of the aorta in Class III. The probability of presence of the aorta in Class III may be determined based on the position of the aorta appearing in axial images (for example, axial images $DA_6$, $DA_{n+6}$, $DA_{j+6}$) having a large cross-sectional area of the liver among the plurality of axial images $DA_1$ to $DA_k$ (see FIG. 7) used to create the classification map CM. A region RM3 in the probability distribution model M3 represents a region having a high probability of presence of the aorta. Referring to an a-a cross section of the probability distribution model M3, it is shown that the probability of presence of the aorta increases from an outer periphery of the region RM3 toward the inside thereof.

The probability distribution model M4 represents the probability of presence of the aorta in Class IV. The probability of presence of the aorta in Class IV may be determined based on the position of the aorta appearing in axial images (for example, axial images $DA_n$, $DA_{n+a}$, $DA_k$) intersecting the liver and kidneys among the plurality of axial images $DA_1$ to $DA_k$ (see FIG. 7) used to create the classification map CM. A region RM4 in the probability distribution model M4 represents a region having a high probability of presence of the aorta. Referring to an a-a cross section of the probability distribution model M4, it is shown that the probability of presence of the aorta increases from an outer periphery of the region RM4 toward the inside thereof.

The search-region defining unit 103 defines a search region for searching for the aorta in the axial images $D_1$ to $D_{10}$ based on the probability distribution models M1 to M4. Now a method of defining a search region in the axial images $D_1$ to $D_{10}$ will be described below. Since the method of defining a search region in the axial images $D_1$ to $D_{10}$ is the same for all the axial images, the axial image $D_1$ is chosen from the axial images $D_1$ to $D_{10}$ to describe the method of defining a search region in the following description.

Figure 25:
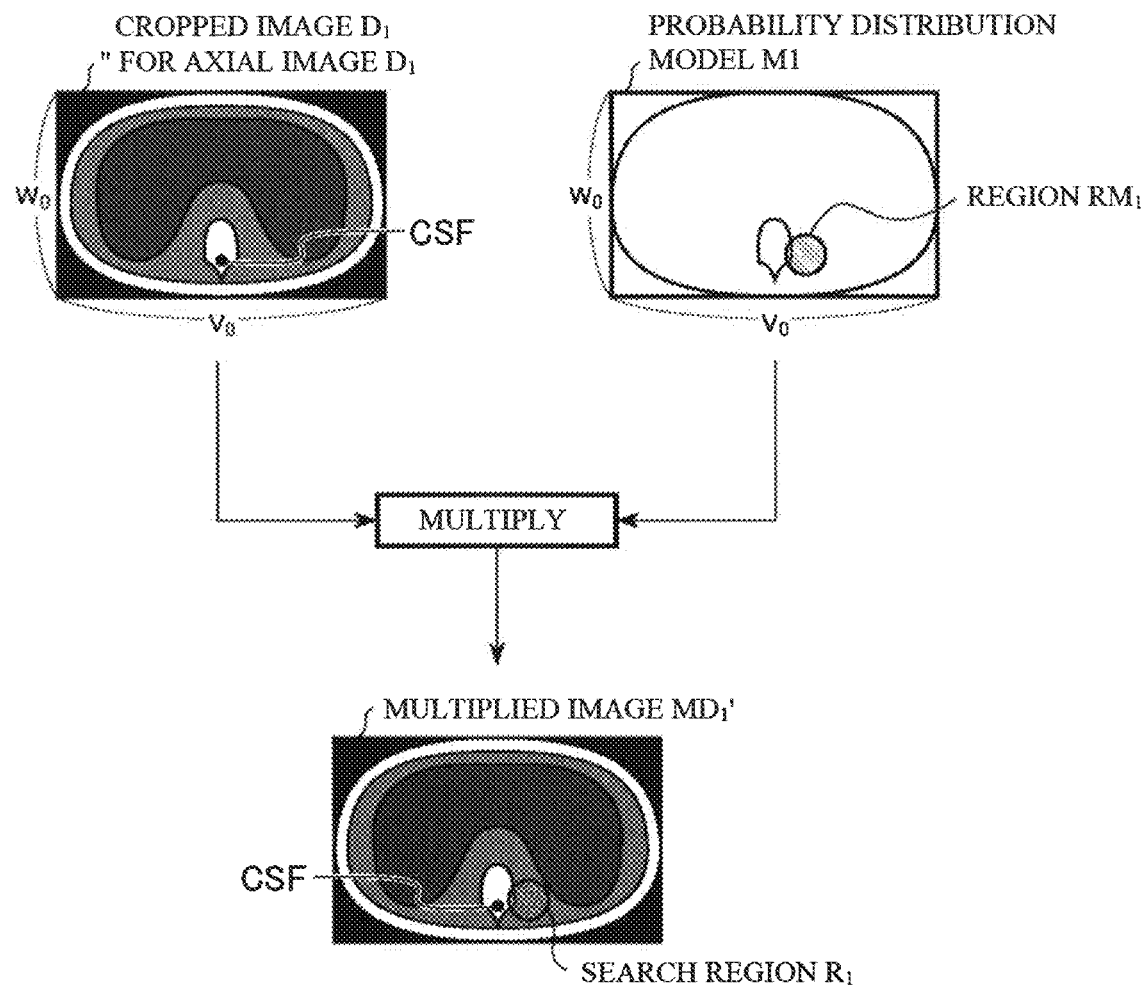
FIG. 25 is a diagram explaining a method of defining a search region.

FIG. 25 is a diagram explaining the method of defining a search region. The search-region defining unit 103 selects a probability distribution model used to determine a search region in the axial image $D_1$ from among the probability distribution models M1 to M4. Since the axial image $D_1$ is classified into Class I (see FIG. 23), the search-region defining unit 103 selects the probability distribution model M1 corresponding to Class I from among the probability distribution models M1 to M4.

Next, the search-region defining unit 103 multiplies the clopped image $D_1'$ (see FIG. 18) obtained from the axial image $D_1$ by the probability distribution model M1 to obtain a multiplied image $MD_1'$.

After obtaining the multiplied image $MD_1'$, the search-region defining unit 103 determines a region R1 corresponding to the region RM1 in the probability distribution model M1 from within the multiplied image $MD_1'$ based on the information on the position of the region RM1 in the probability distribution model M1. The thus-determined region R1 is defined as the aorta search region $R_1$ in the axial image $D_1$.

Figure 26:
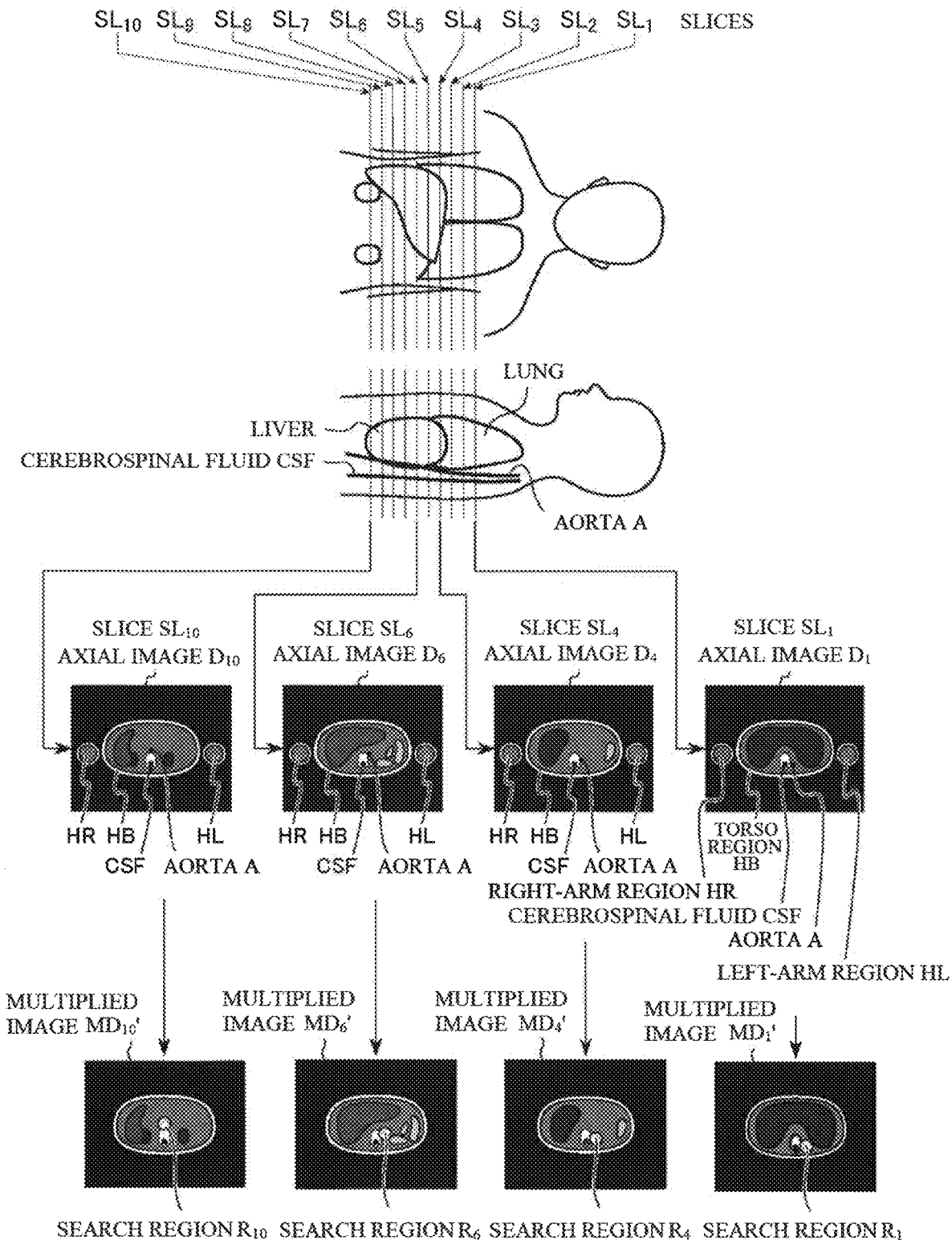
FIG. 26 is a diagram schematically showing multiplied images $MD_1'$ to $MD_{10}'$ and search regions $R_1$ to $R_{10}$ determined for the axial images $D_1$ to $D_{10}$.

While the method of defining the aorta search region $R_1$ in the axial image $D_1$ is explained in FIG. 25, a search region is determined for each of the other axial images $D_2$ to $D_{10}$ as well by determining a multiplied image according to a similar procedure. FIG. 26 schematically shows multiplied images $MD_1'$ to $MD_{10}'$ and search regions $R_1$ to $R_{10}$ determined for the axial images $D_1$ to $D_{10}$. In FIG. 26, multiplied images $MD_1'$, $MD_4'$, $MD_6'$, and $MD_{10}'$ and search regions $R_1$, $R_4$, $R_6$, and $R_{10}$ determined for the four representative axial images $D_1$, $D_4$, $D_6$, and $D_{10}$ among the axial images $D_1$ to $D_{10}$ are schematically shown. After determining the search regions $R_1$ to $R_{10}$, the flow goes to Step ST4.

At Step ST4, the detecting unit 104 (see FIG. 2) detects a position of the aorta from within the search region R1. Now a method of detecting a position of the aorta will be described below. Since the method of detecting a position of the aorta in the axial images $D_1$ to $D_{10}$ is the same for all the axial images, the axial image $D_1$ is chosen from the axial images $D_1$ to $D_{10}$ to describe the method of detecting a position of the aorta in the following description.

Figure 27:
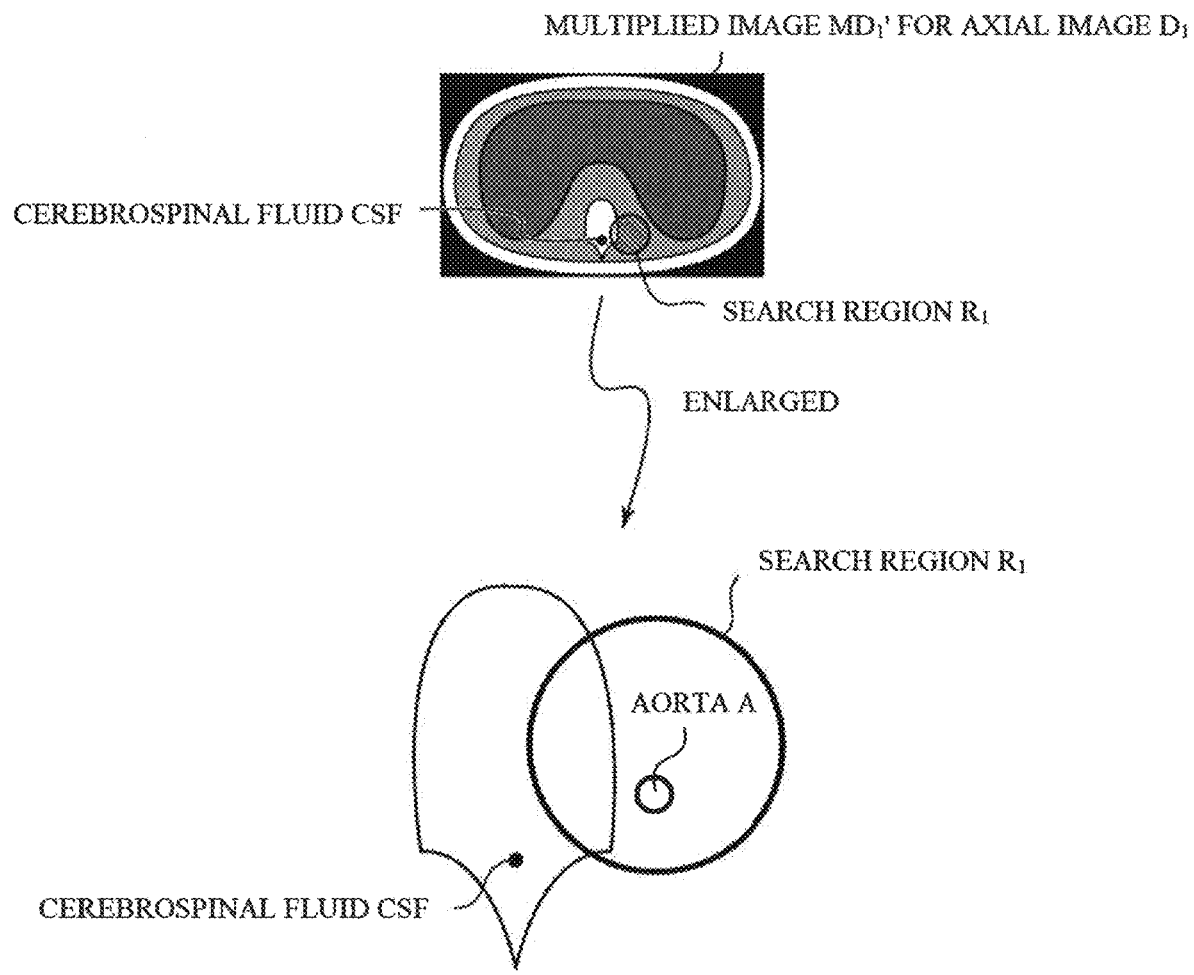
FIG. 27 is a diagram showing a position of a detected cerebrospinal fluid CSF.

At Step ST4, a cerebrospinal fluid CSF is first detected from within the multiplied image $MD_1'$ for the axial image $D_1$. A method of detecting a cerebrospinal fluid CSF that may be employed is, for example, one described in "Med. Imag. Tech., Vol. 31, No. 2, March 2013." FIG. 27 shows a position of the detected cerebrospinal fluid CSF.

Figure 28:
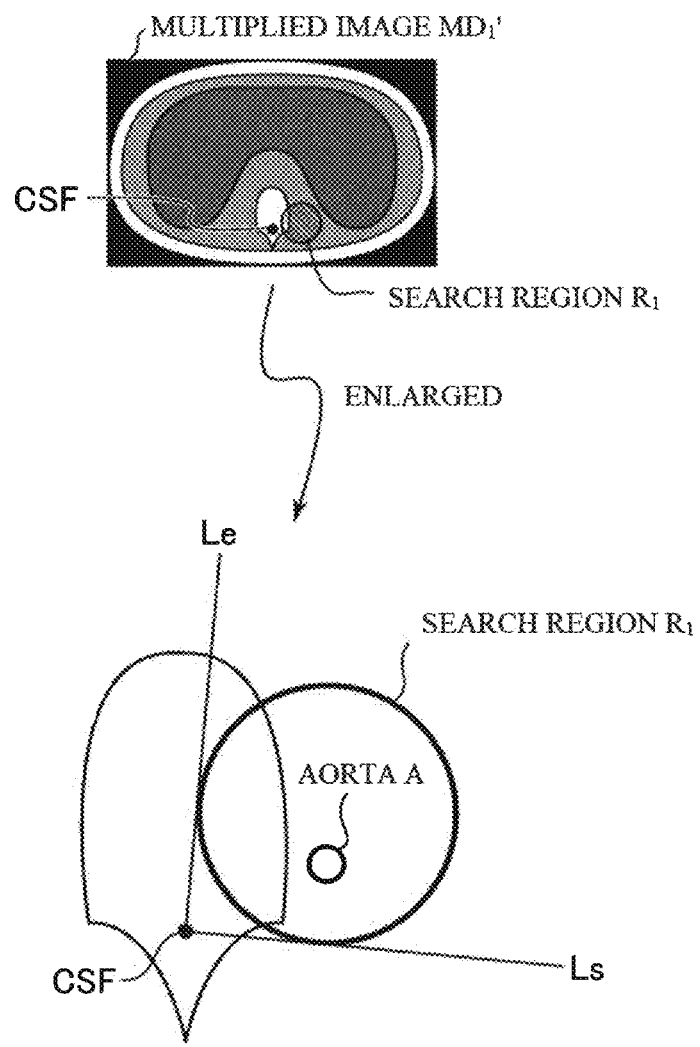
FIG. 28 is a diagram showing lines Ls and Le.

After detecting the cerebrospinal fluid CSF, the detecting unit 104 defines lines Ls and Le tangent to the search region R1 with respect to the cerebrospinal fluid CSF. FIG. 28 shows the lines Ls and Le.

Figure 29:
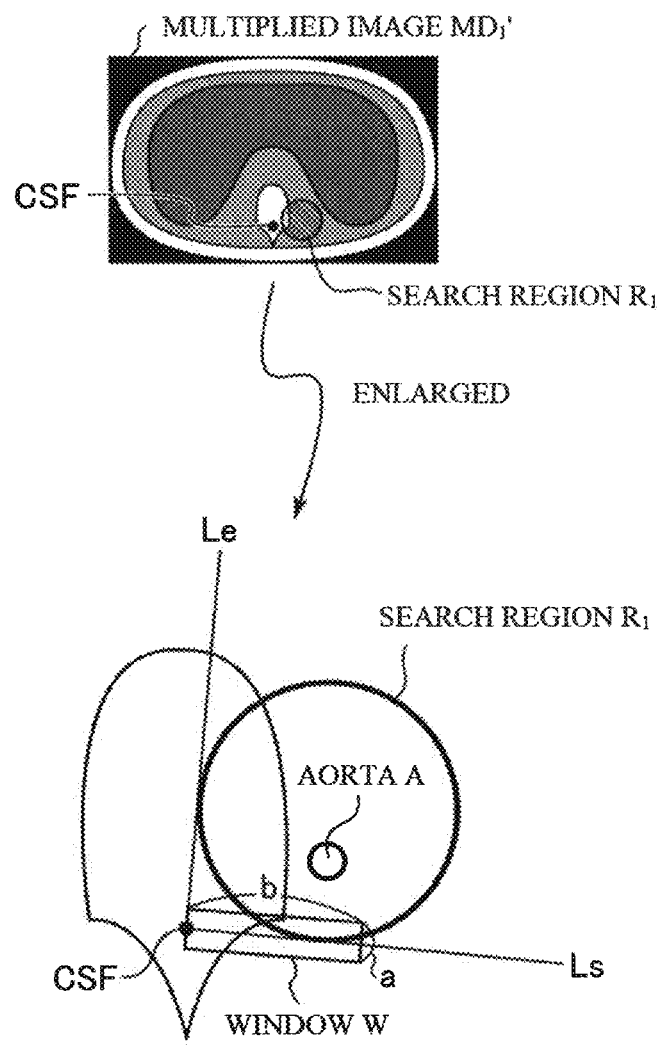
FIG. 29 is a diagram showing a window W.

After defining the lines Ls and Le, the detecting unit 104 defines a window on the line Ls for use in detecting the aorta A (see FIG. 29).

FIG. 29 is a diagram showing a window W defined. The size of the window W is represented by a number of pixels of a by b. The detecting unit 104 defines the window W on the line Ls with respect to the cerebrospinal fluid CSF. After defining the window W, the detecting unit 104 changes a rotation angle θ of the window W by rotating the window W around the cerebrospinal fluid CSF within a range delineated by the lines Ls and Le, and moreover changes the size (the numbers a and b of pixels) of the window W. It then detects the aorta A from within the search region R1 using a classifier C (see FIG. 30), which will be discussed below.

Figure 30:
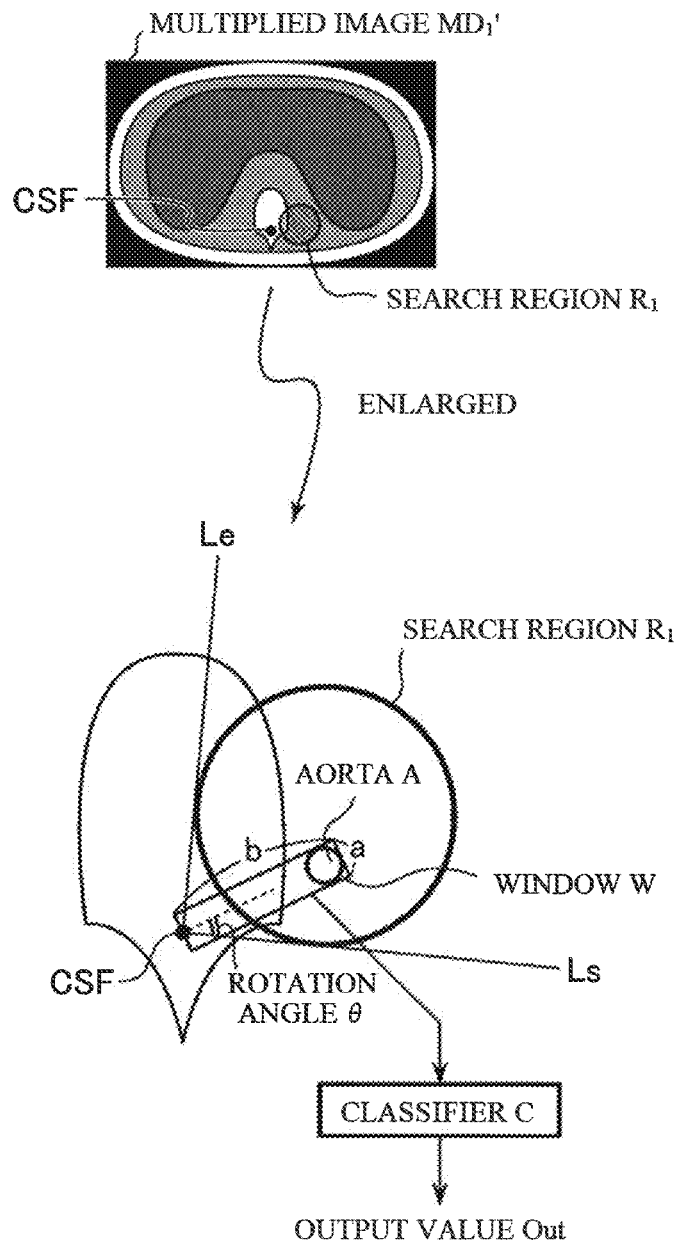
FIG. 30 is an explanatory diagram wherein an aorta A is detected using a classifier C.

FIG. 30 is an explanatory diagram wherein the aorta A is detected using a classifier C. The detecting unit 104 changes θ between θ1 and θ2, and changes values of a and b for the window W each time θ is changed. Then, each time any one of the three parameters (θ, a, b) for the window W is changed, data for pixels in the window W is extracted. The classifier C is for outputting an output value Out for deciding whether the possibility that the aorta A in the axial image $D_1$ inscribes a distal portion of the window W is high or low based on the extracted data, and the classifier C is created in advance before imaging the subject. The classifier C may be created by, for example, learning training data containing information on a signal value for the aorta, and training data containing information on a signal value for a tissue different from the aorta. In the present embodiment, the classifier C is configured so that the output value Out is greater for a higher possibility that the aorta A inscribes the distal portion of the window W. Therefore, it may be decided that the possibility that the aorta A in the axial image $D_1$ inscribes the distal portion of the window W is highest when the output value Out from the classifier C is largest. Assume here that the output value Out from the classifier C is largest when the rotation angle θ=θ$_1$, the number a of pixels=a$_1$, and the number b of pixels=b$_1$. It is then decided that the aorta A in the axial image $D_1$ inscribes the distal portion of the window W when the parameters (θ, a, b) for the window W=(θ$_1$, a$_1$, b$_1$), and thus, the aorta A may be detected from within the search region R1.

Figure 31:
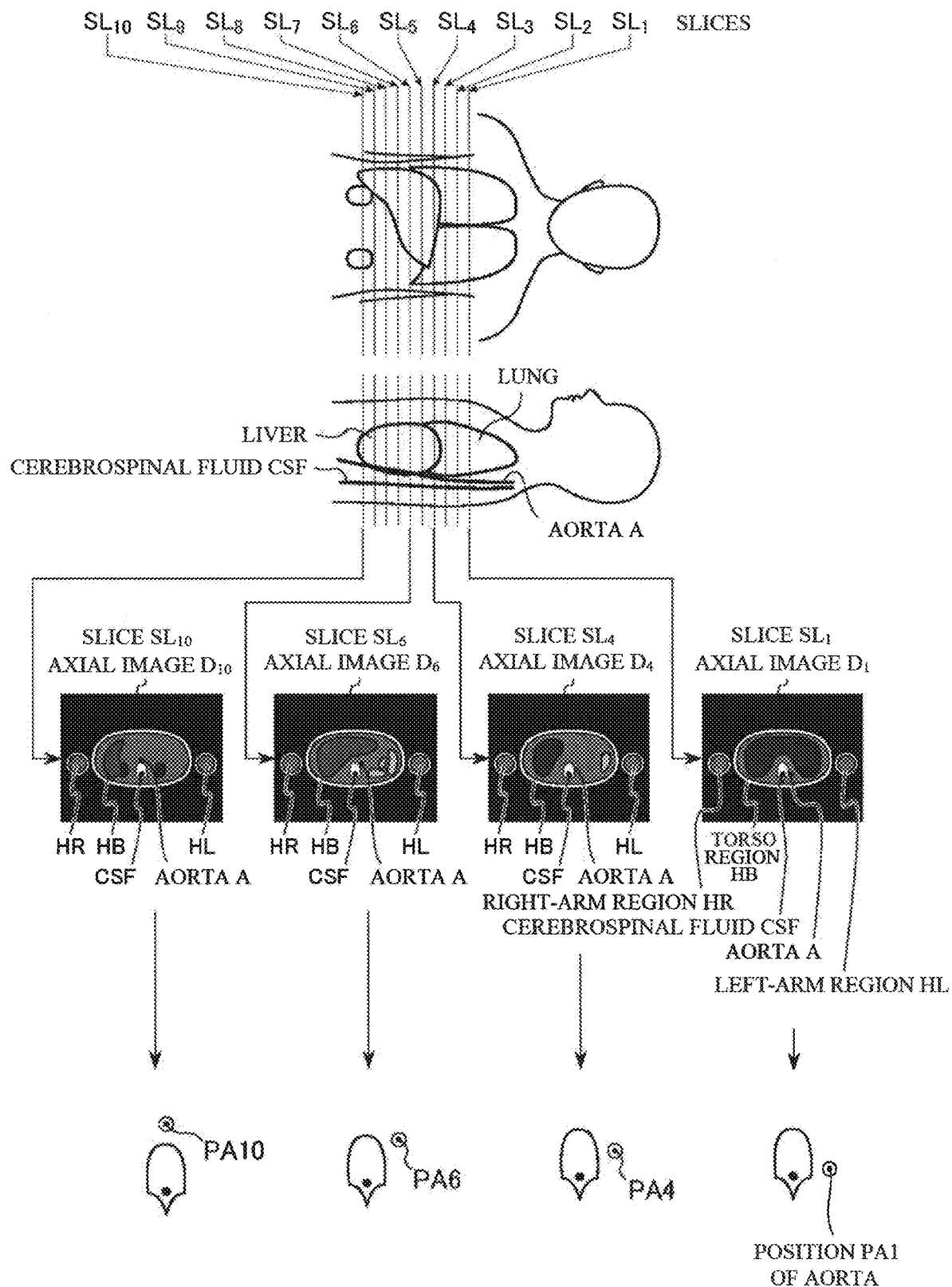
FIG. 31 is a diagram schematically showing positions PA1 to PA10 of the aorta located respectively for the axial images $D_1$ to $D_{10}$ according to Step ST2.

While the method of detecting the aorta A in the axial image $D_1$ is explained in the preceding description, the aorta is detected from within the search region using the classifier C for the other axial images $D_2$ to $D_{10}$ as well. Thus, the position of the aorta may be located for the axial images. FIG. 31 schematically shows positions PA1 to PA10 of the aorta located according to Step ST2 respectively for the axial images $D_1$ to $D_{10}$. The positions PA1 to PA10 of the aorta are not necessarily the center of the aorta, and may lie in the inside of the cross section of the aorta. After locating the position of the aorta in each of the axial images $D_1$ to $D_{10}$, the flow goes to Step ST5.

At Step ST5, the plane calculating unit 105 (see FIG. 2) calculates a plane longitudinally cutting the aorta based on the positions PA1 to PA10 of the detected aorta A. Now a method of calculating the plane will be described below.

First, based on the positions PA1 to PA10 of the aorta, the plane calculating unit 105 identifies a region of a cross section of the aorta on an axial image-by-axial image basis. A method of identifying a region of the cross section of the aorta that may be employed is, for example, a segmentation technique such as a Level Set method. After identifying the region of the cross section of the aorta, a center of the cross section of the aorta is located. For example, a centroid of the cross section of the aorta A may be located as a center of the aorta A. The center of the aorta A may be located by considering the cross section of the aorta A to have a generally circular shape.

Figure 32:
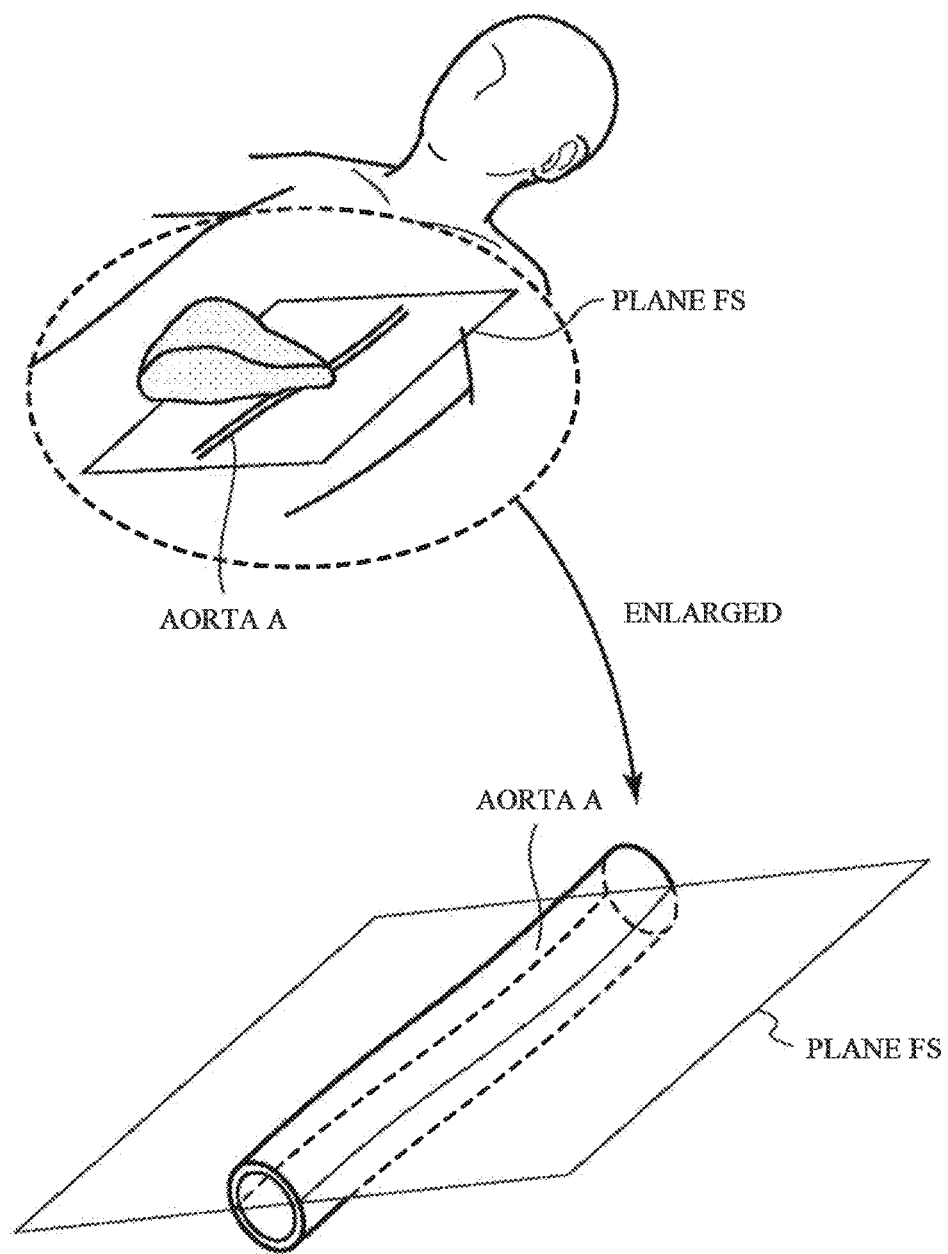
FIG. 32 is a diagram schematically showing a plane FS.

After locating the center of the aorta A, the plane calculating unit 105 determines a plane FS longitudinally cutting the aorta A generally in parallel with a direction of the course of the aorta A based on the information on the position of the center of the aorta A located for each of the axial images $D_1$ to $D_{10}$. FIG. 32 schematically shows the determined plane FS. In the present embodiment, the plane calculating unit 105 calculates a square sum of the distance between the center of the aorta A located for each of the axial images $D_1$ to $D_{10}$ and the plane, and determines as the plane FS a plane when the square sum is minimized. After determining the plane FS, the flow goes to Step ST4.

At Step ST4, a tracker region for detecting a contrast medium is defined. Now a method of defining the tracker region will be described below.

Figure 33:
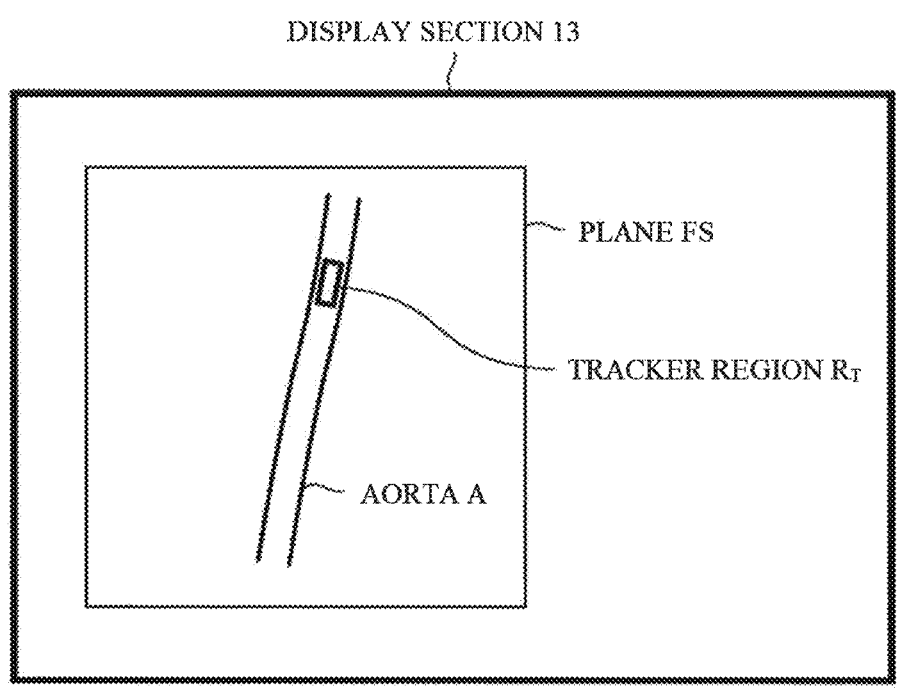
FIG. 33 is a diagram explaining an exemplary method of defining a tracker region.

FIG. 33 is a diagram explaining an exemplary method of defining a tracker region. The operator operates the operating section 12 (see FIG. 1) to input a command for displaying the plane FS determined at Step ST3 in the display section 13. Once the command has been input, the plane FS determined at Step ST3 is displayed in the display section 13.

After the plane FS is displayed, the operator operates the operating section 12 to input information for defining a tracker region referring to a positional relationship among organs and the aorta displayed in the plane FS. Once the information has been input, the tracker-region defining unit 106 (see FIG. 2) defines a tracker region based on the input information. FIG. 32 shows a case in which a tracker region $R_t$ is defined to lie in the inside of the aorta A. It should be noted that the tracker region $R_t$ may be automatically defined based on the position of the aorta A. After defining the tracker region $R_t$, the flow goes to Step ST5.

At Step ST5, a main scan MS (see FIG. 3) is performed. In the main scan MS, the subject is injected with a contrast medium, and a sequence for detecting the contrast medium from the tracker region $R_t$ is repetitively performed. Once a predefined amount of the contrast medium has been injected in the tracker region $R_t$, a scan for acquiring an image of the liver is performed, and the flow is terminated.

In the present embodiment, within which class an axial image falls is determined, and a probability distribution model corresponding to that class is used to determine an aorta search region. Therefore, detection of an aorta may be achieved while focusing upon a region having a high probability of presence of the aorta, thus improving accuracy of detection of the aorta.

Moreover, in the present embodiment, an image portion is clopped from each of the axial images $D_1$ to $D_{10}$ so as to circumscribe the torso region HB, and classification of the axial images $D_1$ to $D_{10}$ is performed. Therefore, the axial images $D_1$ to $D_{10}$ may be classified without being affected by the signal value in the left-arm region HL and right-arm region HR, thus fully reducing a risk that the axial images are wrongly classified.

While the window W is defined with respect to the cerebrospinal fluid CSF in the present embodiment, the window W may be defined with respect to a body part different from the cerebrospinal fluid CSF. Moreover, while the aorta A is detected in the present embodiment, the present invention may be applied to a case in which a blood vessel different from the aorta A is to be detected.

While the present embodiment detects an aorta based on an axial image, the aorta may be determined based on an image in a plane other than the axial plane (for example, an oblique plane intersecting the axial plane at an angle).

While in the present embodiment the window W is rectangular, it may have a different shape (an elliptical shape, for example).

Figure 34:
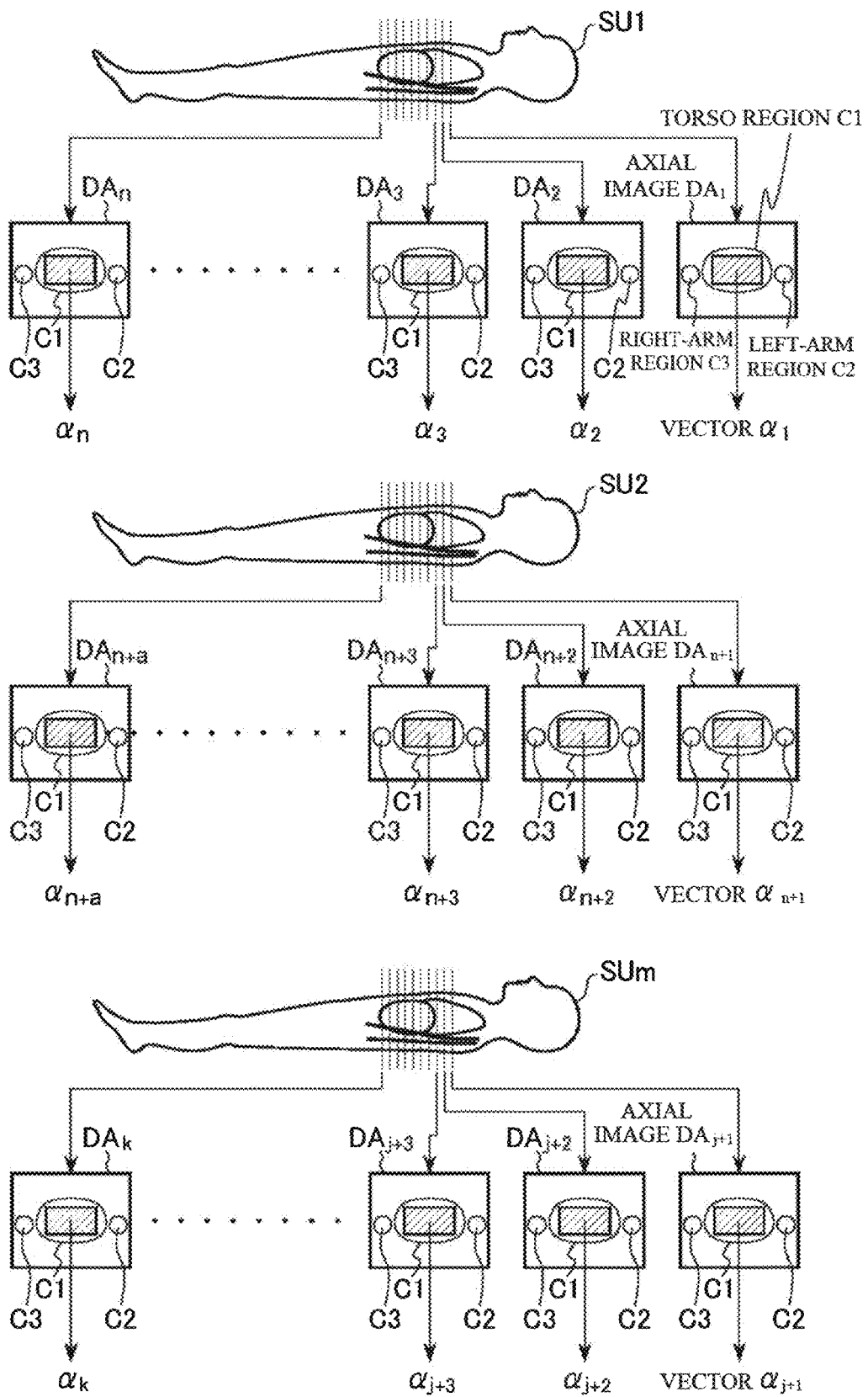
FIG. 34 is a diagram schematically showing an example involving cropping an image portion so that a body surface portion of the torso region C1 is not included, and determining vectors $\alpha_1$ to $\alpha_k$.

In creating the classification map CM in the present embodiment, an image portion in a rectangular region circumscribing the torso region C1 is clopped from each of the axial images (see FIG. 8) to determine vectors $\alpha_1$ to $\alpha_k$ (see FIG. 11). However, the vectors $\alpha_1$ to $\alpha_k$ may be determined by cropping the image portion so that the center portion of the torso region C1 is included and a body surface portion is not included. FIG. 34 is a diagram schematically showing an example involving cropping an image portion so that the body surface portion of the torso region C1 is not included, and determining the vectors $\alpha_1$ to $\alpha_k$. According to the method in FIG. 34, since the vectors $\alpha_1$ to $\alpha_k$ are determined based on the image portion (hatched portion) including the center portion of the torso region C1 and not including the body surface portion, a classification map CM' (not shown) may be created with a reduced effect of fat in the body surface portion. When the classification map CM' is created in place of the classification map CM (see FIG. 13), again, the axial images may be classified by performing Step ST2. When classifying axial images using the classification map CM, an image portion is clopped from the axial image $D_1$ so as to circumscribe the torso region HB at Step ST24. When classifying axial images using the classification map CM' in place of the classification map CM, however, an image portion may be clopped from the axial image $D_1$ so as not to include the body surface portion of the torso region HB at Step ST24.

Furthermore, in the present embodiment, the classification map is created by cropping the image portion so as not to include the left-arm and right-arm regions. However, the classification map may be created by cropping an image portion so as to include the left-arm and right-arm regions insofar as axial images are correctly classified.

While the method of classifying axial images using the Laplacian eigenmaps method is described in the present embodiment, the classification method in the present embodiment is exemplary, and axial images may be classified using any other technique.

What is claimed is:

1. A blood vessel detecting apparatus comprising:
   an image producing unit for producing a plurality of images in a plurality of slices defined in a body part to be imaged containing a blood vessel;
   a classifying unit for classifying said plurality of images into a plurality of classes based on which portion in said imaged body part each of said plurality of images represents;
   a defining unit for defining a search region for searching for said blood vessel from within said image based on within which of said plurality of classes said image falls; and
   a detecting unit for detecting a position of said blood vessel from said search region.

2. The blood vessel detecting apparatus as recited in claim 1, wherein a model representing a probability of presence of said blood vessel is made corresponding to each said class; and said defining unit defines said search region based on said model.

3. The blood vessel detecting apparatus as recited in claim 1, wherein said plurality of classes includes
   a first class corresponding to images having a large cross-sectional area of lungs;
   a second class corresponding to images intersecting a vicinity of a border between the lungs and a liver;
   a third class corresponding to images having a large cross-sectional area of the liver; and
   a fourth class corresponding to images intersecting the liver and kidneys.

4. The blood vessel detecting apparatus as recited in claim 1, wherein said classifying unit classifies said plurality of images into a plurality of classes based on a map for identifying which portion of said imaged body part each of said plurality of images represents.

5. The blood vessel detecting apparatus as recited in claim 4, wherein said classifying unit determines a vector whose elements are pixel values of pixels in said image, maps a point corresponding to said image onto said map based on said vector, and determines within which of said plurality of classes said image falls based on a position at which said point is mapped in said map.

6. The blood vessel detecting apparatus as recited in claim 5, wherein each of said plurality of images includes a first region representing a cross-section of a torso of a subject, a second region representing a cross-section of a left arm of said subject, and a third region representing a cross-section of a right arm of said subject; and said classifying unit clops from said image an image portion that includes said first region and does not include said second region nor said third region, and determines said vector based on an image obtained by cropping said image portion.

7. The blood vessel detecting apparatus as recited in claim 5, wherein each of said plurality of images includes a first region representing a cross-section of a torso of a subject, a second region representing a cross-section of a left arm of said subject, and a third region representing a cross-section of a right arm of said subject; and said classifying unit crops from said image an image portion that includes a central portion of said first region and does not include a body surface portion of said first region, said second region, nor said third region, and determines said vector based on an image obtained by cropping said image portion.

8. A program for causing a computer to execute:
   image producing processing of producing a plurality of images in a plurality of slices defined in a body part to be imaged containing a blood vessel;
   classifying processing of classifying said plurality of images into a plurality of classes based on which portion in said imaged body part each of said plurality of images represents;
   defining processing of defining a search region for searching for said blood vessel from within said image based on within which of said plurality of classes said image falls; and
   detecting processing of detecting a position of said blood vessel from said search region.

9. A blood vessel detecting apparatus comprising:
   an image producing unit for producing a plurality of images in a plurality of slices defined in a body part to be imaged containing a blood vessel;
   a classifying unit for classifying said plurality of images into a plurality of classes based on which portion in said imaged body part each of said plurality of images represents;
   a defining unit for defining a search region for searching for said blood vessel from within said image based on within which of said plurality of classes said image falls; and
   wherein a model representing a probability of presence of said blood vessel is made corresponding to each said class; and said defining unit defines said search region based on said model.

* * * * *